US00RE45763E

(19) United States
(12) Reissued Patent
Brophy et al.

(10) Patent Number: US RE45,763 E
(45) Date of Reissued Patent: Oct. 20, 2015

(54) ANTIBODIES TO TROPONIN I AND METHODS OF USE THEREOF

(71) Applicants: Susan E. Brophy, Grayslake, IL (US); Bailin Tu, Libertyville, IL (US); Dagang Huang, Mundelein, IL (US); Lowell J. Tyner, Chicago, IL (US); Robert N. Ziemann, Palatine, IL (US)

(72) Inventors: Susan E. Brophy, Grayslake, IL (US); Bailin Tu, Libertyville, IL (US); Dagang Huang, Mundelein, IL (US); Joan D. Tyner; Robert N. Ziemann, Palatine, IL (US)

(73) Assignee: Abbott Laboratories, Abbott Park, IL (US)

(21) Appl. No.: 14/035,420

(22) Filed: Sep. 24, 2013

Related U.S. Patent Documents

Reissue of:

(64) Patent No.: 8,030,026
Issued: Oct. 4, 2011
Appl. No.: 12/391,937
Filed: Feb. 24, 2009

(51) Int. Cl.

| | |
|---|---|
| ***C12P 21/04*** | (2006.01) |
| ***C12P 21/06*** | (2006.01) |
| ***C12N 5/00*** | (2006.01) |
| ***C12N 5/07*** | (2010.01) |
| ***C07H 21/04*** | (2006.01) |
| ***C07K 16/18*** | (2006.01) |
| ***C07K 14/47*** | (2006.01) |

(52) U.S. Cl.
CPC ..... *C07K 16/18* (2013.01); *C07K 14/4716* (2013.01); *C07K 2317/24* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,526,938 | A | 7/1985 | Churchill |
| 4,816,397 | A | 3/1989 | Boss |
| 4,816,567 | A | 3/1989 | Cabilly |
| 4,880,078 | A | 11/1989 | Inoue |
| 5,006,309 | A | 4/1991 | Khalil |
| 5,063,081 | A | 11/1991 | Cozzette |
| 5,089,424 | A | 2/1992 | Khalil |
| 5,128,326 | A | 7/1992 | Balazs |
| 5,223,409 | A | 6/1993 | Ladner |
| 5,225,539 | A | 7/1993 | Winter |
| 5,290,540 | A | 3/1994 | Prince |
| 5,530,101 | A | 6/1996 | Queen |
| 5,565,332 | A | 10/1996 | Hoogenboom |
| 5,565,352 | A | 10/1996 | Hochstrasser |
| 5,585,089 | A | 12/1996 | Queen |
| 5,624,821 | A | 4/1997 | Winter |
| 5,648,260 | A | 7/1997 | Winter |
| 5,679,377 | A | 10/1997 | Berstein |
| 5,693,762 | A | 12/1997 | Queen |
| 5,705,330 | A | 1/1998 | Shah |
| 5,714,350 | A | 2/1998 | Co |
| 5,714,352 | A | 2/1998 | Jakobovits |
| 5,723,323 | A | 3/1998 | Kauffman |
| 5,763,192 | A | 6/1998 | Kauffman |
| 5,766,886 | A | 6/1998 | Studnicka |
| 5,807,715 | A | 9/1998 | Morrison |
| 5,814,476 | A | 9/1998 | Kauffman |
| 5,817,483 | A | 10/1998 | Kauffman |
| 5,824,514 | A | 10/1998 | Kauffman |
| 5,855,913 | A | 1/1999 | Hanes |
| 5,874,064 | A | 2/1999 | Edwards |
| 5,912,015 | A | 6/1999 | Bernstein |
| 5,912,120 | A | 6/1999 | Goldstein |
| 5,916,597 | A | 6/1999 | Lee |
| 5,934,272 | A | 8/1999 | Lloyd |
| 5,976,862 | A | 11/1999 | Kauffman |
| 5,985,309 | A | 11/1999 | Edwards |
| 5,985,320 | A | 11/1999 | Edwards |
| 5,989,463 | A | 11/1999 | Tracy |
| 6,019,968 | A | 2/2000 | Platz |
| 6,180,370 | B1 | 1/2001 | Queen |
| 6,194,222 | B1 * | 2/2001 | Buechler et al. ..... 436/518 |
| 6,204,023 | B1 | 3/2001 | Robinson |
| 6,350,861 | B1 | 2/2002 | Co |
| 6,699,658 | B1 | 3/2004 | Wittrup |
| 7,285,418 | B2 | 10/2007 | Katrukha |
| 7,371,383 | B2 * | 5/2008 | Reed et al. ..... 424/145.1 |
| 8,030,026 | B2 | 10/2011 | Brophy et al. |
| 2002/0137134 | A1 | 9/2002 | Gerngross |
| 2003/0170881 | A1 | 9/2003 | Davis |
| 2003/0186374 | A1 | 10/2003 | Hufton |
| 2004/0018577 | A1 | 1/2004 | Campbell |
| 2004/0018590 | A1 | 1/2004 | Gerngross |
| 2005/0054078 | A1 | 3/2005 | Miller |
| 2006/0018897 | A1 | 1/2006 | Lee |
| 2006/0160164 | A1 | 7/2006 | Miller |

FOREIGN PATENT DOCUMENTS

| | | | |
|---|---|---|---|
| EP | 86631 | A2 | 8/1983 |
| EP | 229246 | | 7/1987 |
| EP | 0229246 | A2 | 7/1987 |
| EP | 239400 | | 9/1987 |
| EP | 0239400 | A2 | 9/1987 |
| EP | 519596 | | 12/1992 |
| EP | 0519596 | A1 | 12/1992 |
| EP | 592106 | | 7/1993 |
| EP | 239400 | | 3/1994 |
| EP | 592106 | | 4/1994 |

(Continued)

OTHER PUBLICATIONS

Eriksson et al. (2005) "Comparison of Cardiac Troponin I Immunoassays Variably Affected by Circulating Autoantibodies," Clin. Chem. 51(5):848-855.

(Continued)

*Primary Examiner* — Shulamith H Shafer
(74) *Attorney, Agent, or Firm* — Lisa V. Mueller; Michael Best & Friedrich LLP

(57) ABSTRACT

The subject invention relates to antibodies to troponin I as well as methods of use thereof. In particular, such antibodies may be used to detect Troponin I in a patient and may also be used in the diagnosis of, for example, a myocardial infarction or acute coronary syndrome.

10 Claims, 16 Drawing Sheets

(56) References Cited

FOREIGN PATENT DOCUMENTS

| | | | |
|---|---|---|---|
| EP | 0592106 | A1 | 4/1994 |
| EP | 0239400 | B1 | 8/1994 |
| EP | 1176195 | | 1/2002 |
| EP | 1176195 | A1 | 1/2002 |
| EP | 519596 | | 2/2005 |
| EP | 0519596 | B1 | 2/2005 |
| EP | 2014302 | A1 | 1/2009 |
| FR | 2779526 | A1 | 12/1999 |
| GB | 8901334 | | 5/1990 |
| GB | 9101134 | | 1/1992 |
| GB | 9201755 | | 4/1993 |
| WO | 9005144 | | 5/1990 |
| WO | 9005144 | A1 | 5/1990 |
| WO | 9005370 | A1 | 5/1990 |
| WO | 9001443 | A1 | 11/1990 |
| WO | 9014424 | | 11/1990 |
| WO | 9014424 | A1 | 11/1990 |
| WO | 9014430 | | 11/1990 |
| WO | 9014430 | A1 | 11/1990 |
| WO | 9014443 | | 11/1990 |
| WO | 9105548 | | 5/1991 |
| WO | 9105548 | A1 | 5/1991 |
| WO | 9105939 | | 5/1991 |
| WO | 9105939 | A1 | 5/1991 |
| WO | 9109630 | | 7/1991 |
| WO | 9109630 | A1 | 7/1991 |
| WO | 9109967 | | 7/1991 |
| WO | 9109967 | A1 | 7/1991 |
| WO | 9117271 | | 11/1991 |
| WO | 9117271 | A1 | 11/1991 |
| WO | 9201047 | | 1/1992 |
| WO | 9201047 | A1 | 1/1992 |
| WO | 9209690 | | 6/1992 |
| WO | 9209690 | A2 | 6/1992 |
| WO | 9215679 | | 9/1992 |
| WO | 9215679 | A1 | 9/1992 |
| WO | 9218619 | | 10/1992 |
| WO | 9218619 | A1 | 10/1992 |
| WO | 9219244 | | 11/1992 |
| WO | 9219244 | A2 | 11/1992 |
| WO | 9220791 | | 11/1992 |
| WO | 9220791 | A1 | 11/1992 |
| WO | 9301288 | | 1/1993 |
| WO | 9301288 | A1 | 1/1993 |
| WO | 9306213 | A1 | 4/1993 |
| WO | 9401234 | | 1/1994 |
| WO | 9401234 | A2 | 1/1994 |
| WO | 9601878 | A1 | 6/1996 |
| WO | 9618978 | | 6/1996 |
| WO | 9620698 | | 7/1996 |
| WO | 9620698 | A2 | 7/1996 |
| WO | 9729131 | | 8/1997 |
| WO | 9729131 | A1 | 8/1997 |
| WO | 9732572 | | 9/1997 |
| WO | 9732572 | A2 | 9/1997 |
| WO | 9744013 | | 11/1997 |
| WO | 9744013 | A1 | 11/1997 |
| WO | 9816280 | | 4/1998 |
| WO | 9831346 | | 7/1998 |
| WO | 9831346 | A1 | 7/1998 |
| WO | 9915154 | | 4/1999 |
| WO | 9915154 | A1 | 4/1999 |
| WO | 9920253 | | 4/1999 |
| WO | 9920253 | A1 | 4/1999 |
| WO | 9954342 | | 10/1999 |
| WO | 9954342 | A1 | 10/1999 |
| WO | 9966903 | | 12/1999 |
| WO | 9966903 | A2 | 12/1999 |
| WO | 0183525 | | 11/2001 |
| WO | 0183525 | A2 | 11/2001 |
| WO | 02072636 | | 9/2002 |
| WO | 02072636 | A2 | 9/2002 |
| WO | 03016466 | | 2/2003 |
| WO | 03016466 | A2 | 2/2003 |
| WO | 03035835 | | 5/2003 |
| WO | 03035835 | A2 | 5/2003 |
| WO | 2005000901 | A2 | 1/2005 |
| WO | WO2005000901 | | 1/2005 |
| WO | 2005100584 | | 10/2005 |
| WO | 2005100584 | A2 | 10/2005 |

OTHER PUBLICATIONS

Hytest 1999 Product Catalog.
Hytest 2000 General Product Catalog.
Hytest 2001 Cardiac Markers Panel.
Hytest 2001-2002 General Product Catalog.
Hytest 2003 General Product Catalog.
Hytest 2004 Cardiac Markers Panel.
Hytest 2004-2005 General Product Catalog.
Hytest 2005 Markers of Cardiovascular Diseases Catalog.
Hytest 2005-2006 General Product Catalog.
Hytest 2006-2007 General Product Catalog.
Hytest 2007 Markers of Cardiovascular Diseases Catalog.
Hytest 2007-2008 General Product Catalog.
Hytest 2008-2009 General Product Catalog.
Katrukha (2006) "Troponin I measurement: the concept of a precise immunoassay," Clin. Lab. Internat. 30(5):14-16.
Katrukha et al. (1998) "Degradation of cardiac troponin I: implication for reliable immunodetection," Clin. Chem. 44 (12):2433-2440.
Reverse Translate a Protein (www.vivo.colostae.edu/molkit/translate/index.html), Last updated on Jun. 20, 1998 (Exhibit AA).
Table showing Codon-amino acid Abbreviations (www.hgmd.cf.ac.uk/docs/cd_amino.html) (Exhibit BB).
Ylikotila et al. (2006) "Utilization of Recombinant Fab Fragments in a cTnI Immunoassay Conducted in Spot Wells," Clin. Biochem. 39:843-850.
Lam, et al., "Microencapsulation of Recombinant Humanized Monoclonal Antibody for Local Delivery," Proc. Int'l Symp. Control Rel. Bioact. Mater., vol. 24 pp. 759-760 (1997).
Langer, et al,. J. Macromol. Sci. Rev. Macromol. Chem., vol. 23 p. 61 (1983).
Medical Applications of Controlled Release, Langer and Wise (eds), CRC Press, Boca Raton, Florida (1974).
Padlan, et al., Molecular Immunology, vol. 28 (4/5) pp. 489-498 (1991).
Quinn, F., et al., The Immunoassay Handbook, 2.sup.nd Edition, pp. 363-367 (2001). Riechmann, et al., Nature, vol. 332 p. 323 (1988).
Sambrook, et al., A Laboratory Manual, Molecular Cloning, 2.sup.nd Edition, Cold Spring Harbor Laboratory Press, Cold Spring Harbor, New York (1989).
Rudikoff et al Proc. Natl. Acad. Sci.USA, 79(6):1979-1983, Mar. 1982.
Giege, R., et al., Crystallization of Nucleic Acids and Proteins , a Practical Approach, 2.sup.nd Edition, pp. 20 1-16, Oxford University Press, New York, New York (1999).
Jefferis, R., et al., Biotechnol. Prog., vol. 21 pp. 11-16 (2005).
Kabat, et al., Ann. NY Acad. Sci., vol. 190 pp. 382-391 (1971).
Kabat, et al., Sequences of Proteins of Immunological Interest, 5.sup.th Edition, Department of Health and Human Services, NIH Publication No. 91/3242, USA (1991).
Hytest 2008 Markers of Cardiovascular Diseases and Metabolic Syndrome.
Paul, Fundamental Immunology, 3rd Edition, 1993, pp. 292-295, under the heading "Fv Structure and Diversity in Three Dimensions".*
Rudikoff et al Proc. Natl. Acad. Sci.USA, 76(6):1979-1983, Mar. 1982.*
Colman P. M. Research in Immunology, 145:33-36, 1994.*
Filatov V. L., et al., "Epitope Mapping of Anti-Troponin I Monoclonal Antibodies, XP000941112," Biochemistry and Molecular Biology International, 36039, 45 (6), Academic Press, London, GB, 1179-1187.
PCT International Search Report and Written Opinion of International Application No. PCT/US2010/024979 mailed on May 6, 2010, 21 pages.

(56) References Cited

OTHER PUBLICATIONS

Peronnet, et al., "Isoelectric point determination of cardiac troponin I forms present 1n plasma from patients with myocardial Infarction, NL LNKDD0I: 10.1016/J.CCA.2006.10.006, XP005805375," Clinica Chimica Acta, 39066, 377 (1-2), Elsevier BV, Amsterdam, 243-247.
Rama D., et al., "Epitope Localization of Monoclonal Antibodies Used in Human Troponin I Immunoenzymometric Assay, XP009033257," Hybridoma, 35431, 16 (2), Liebert, New York, NY, US, 153-157.
Altshchul, et al., Nucleic Acids Research, vol. 25 pp. 3389-3402 (1997).
Azzazy, H., et al., Clin. Biochem., vol. 35 pp. 425-445 (2002).
Barbas, et al., PNAS, vol. 88 pp. 7978-7982 (1991).
Bird, et al., Science, vol. 242 pp. 423-426 (1988).
Bodar, et al., Clinical Chemistry, vol. 38 pp. 2203-2214 (1992).
Boder, et al., Nature Biotechnology, vol. 15 pp. 553-557 (Jun. 1997).
Buchwald, et al., Surgery, vol. 88 p. 507 (1980).
Carter, et al., Proc. Natl. Acad. Sci., vol. 89 p. 4285, USA (1992).
Chothia, et al., J. Mol. Biol., vol. 196 pp. 901-917 (1987).
Chothia, et al., J. Mol. Biol., vol. 227 p. 799 (1992).
Chothia, et al., Nature, vol. 342 pp. 877-883 (1989).
Clackson, et al., Nature, vol. 352 pp. 624-628 (1991).
Cleek, et al., "Biodegradable Polymeric Carriers for a bFGF Antibody for Cardiovascular Application," Pro. Int'l. Symp. Control. Rel. Bioact. Mater., vol. 24 pp. 853-854 (1997).
Co, M.S., et al., Mol. Immunol., vol. 30 pp. 1361-1367 (1993).
Controlled Drug Bioavailability, Drug Product Design and Performance, Smolen and Ball (eds), Wiley, New York (1984).
Cummins, et al., Am. Heart Journal, vol. 113 pp. 1333-1344 (1987).
During, et al., Ann. Neurol., vol. 25 p. 351 (1989).
Foote, et al., J. Mol. Biol., vol. 224 pp. 487-499 (1992).
Fuchs, et al., Bio/Technology, vol. 9 pp. 1370-1372 (1991).
Garrad, et al., Bio/Technology, vol. 9 pp. 1373-1377 (1991).
Gavilondo, J.V., et al., BioTechniques, vol. 29 pp. 128-145 (2000).
Giege, R., et al., Crystallization of Nucleic Acids and Proteins , a Practical Approach, 2nd Edition, pp. 20 1-16, Oxford University Press, New York, New York (1999).
Gillies, et al., J. Immunol. Methods, vol. 125 pp. 191-202 (1989).
Goodson, et al., Medical Applications of Controlled Release, supra, vol. 2 pp. 115-138 (1984).
Gram, et al., PNAS, vol. 89 pp. 3576-3580 (1992).
Griffiths, et al., EMBO J., vol. 12 pp. 725-734 (1993).
Hay, et al., Hum. Antibod. Hybridomas, vol. 3 pp. 81-85 (1992).
Hawkins, et al., J. Mol. Biol., vol. 226 pp. 889-896 (1992).
Higgins, et al., CABIOS, 5L151-5L153 (1989).
Holliger, P., et al., Proc. Natl. Acad. Sci., vol. 90 pp. 6444-6448, USA (1993).
Hoogenboom, et al., Nuc. Acid Res., vol. 19 pp. 4133-4137 (1991).
Hoogenboom, H.R., et al., TIB Tech., vol. 15 pp. 62-70 (1997).
Hoogenboom, H., et al., Immunology Today, vol. 21 pp. 371-378 (2000).
Howard, et al., J. Neurosurg., vol. 71 p. 105 (1989).
Huse, et al., Science, vol. 246 pp. 1275-1281 (1989).
Huston, et al., Proc. Natl. Acad. Sci., vol. 85 pp. 5879-5883, USA (1988).
Johnsson, B., et al., J. Mol. Recognit., vol. 8 pp. 125-131 (1995).
Johnsson, B., et al., Anal. Biochem., vol. 198 pp. 268-277 (1991).
Jones, et al., Nature, vol. 321 pp. 522 (1986).
Jönsson, U., et al., Biotechniques, vol. 11 pp. 620-627 (1991).
Jonsson, U., et al. Ann. Biol. Clin. 51: 19-26 (1993).
Kabat, et al., Sequences of Proteins of Immunological Interest, National Institutes of Health, Bethesda, Maryland (1987) and (1991).
Kaufman, R.J., et al., Mol. Biol., vol. 159 pp. 601-621 (1982).
Kellermann, S.A., et al., Current Opinion in Biotechnology, vol. 13 pp. 593-597 (2002).
Kipriyanov, S.M., et al., Human Antibodies and Hybridomas, vol. 6 pp. 93-101 (1995).
Kipriyanov, S.M., et al., Mol. Immunol., vol. 31 pp. 1047-1058 (1994).
Kontermann, Antibody Engineering, p. 790, Springer-Verlag, New York (2001).
Langer, et al., Science, vol. 249 pp. 1527-1533 (1990).
Langer, supra, Sefton, et al., CRC Crit. Ref. Biomed. Eng., vol. 14 p. 20 (1987).
Levy, et al., Science, vol. 228 p. 190 (1985).
Little, M., et al., Immunology Today, vol. 21 pp. 364-370 (2000).
MacCallum, et al., J. Mol. Biol., vol. 262 (5) pp. 732-745 (1996).
Marchalonis, et al., Adv. Exp. Med. Biol., vol. 484 pp. 13-30 (2001).
McCafferty, et al., Nature, vol. 348 pp. 552-554 (1990).
Mizushima, et al, Nucleic Acids Research, vol. 18 p. 5322 (1990).
Morrison, et al., Science, vol. 229 p. 1202 (1985).
Morrison, et al., Proc. Natl. Acad. Sci., vol. 81 pp. 851-855 (1984).
Needleman, et al., J. Mol. Biol., vol. 48 p. 443 (1970).
Neuberger, et al., Nature, vol. 312 pp. 604-608 (1984).
Ning, et al., "Intratumoral Radioimmunotherapy of a Human Colon Cancer Xenograft Using a Sustained-Released Gel," Radiotherapy and Oncology, vol. 39 pp. 179-189 (1996).
Oi, et al., BioTechniques, vol. 4 p. 214 (1986).
Padlan, et al., Faseb J., vol. 9 pp. 133-139 (1995).
Pearson, et al., Proc. Natl. Acad. Sci. vol. 85 p. 2444, USA, (1988).
Poljak, R.J., et al., Structure, vol. 2 pp. 1121-1123 (1994).
Presta, et al., J. Immunol., vol. 151 p. 2623 (1993).
Riechmann, et al., Nature, vol. 332 p. 323 (1988).
Roguska, et al., PNAS, vol. 91 pp. 969-973 (1994).
Saudek, et al., N. Engl. J. Med., vol. 321 p. 574 (1989).
Schiestl, et al., Current Genetics, vol. 16 (5-6) pp. 339-346 (Dec. 1989).
Shapiro, et al., Crit. Rev. Immunol., vol. 22 (3) pp. 183-200 (2002).
Shields, R.L., et al,. J. Biol. Chem., vol. 277 pp. 26733-26740 (2002).
Sims, et al., J. Immunol., vol. 151 p. 2296 (1993).
Smith, et al., Appl. Math., vol. 2 p. 482 (1981).
Song, et al., "Antibody Mediated Lung Targeting of Long-Circulating Emulsions," PDA Journal of Pharmaceutical Science and Technology, vol. 50 pp. 372-397 (1995).
Studnicka, et al., Protein Engineering, vol. 7 (6) pp. 805-814 (1994).
Takeda, et al., Nature, vol. 314 pp. 452-454 (1985).
Taylor, L.D., et al., Nucl. Acids Res., vol. 20 pp. 6287-6295 (1992).
Umana, et al., Nat. Biotech., vol. 17 pp. 176-181 (1999).
Urlaub, et al., Proc. Natl. Acad. Sci., vol. 77 pp. 4216-4220, USA (1980).
Verhoeyen, et al., Science, vol. 239 p. 1534 (1988).
Wallick, S.C., et al., Exp. Med., vol. 168 pp. 1099-1109 (1988).
Ward, et al., Nature, vol. 341 pp. 544-546 (1989).
Winnaker, et al., From Genes to Cones, Verlagsgesellschaft, Weinheim, Germany (1987).
Wright, A,. et al., EMBO J., vol. 10 pp. 2717-2723 (1991).
Wu, et al., J. Biol. Chem., vol. 262 pp. 4429-4432 (1987).

* cited by examiner scFv construct used for yeast display engineering

```
                                19C7 Variable Heavy Gene
                    ----------------------------------------------------------
SEQ ID NO: 54   1   GAGGTCCAG CTTCAGCAG TCAGGACCT GACCTGGTG AAACCTGGG GCCTCAGTG
SEQ ID NO: 55       CTCCAGGTC GAAGTCGTC AGTCCTGGA CTGGACCAC TTTGGACCC CGGAGTCAC

                        19C7 Variable Heavy Gene
                    ----------------------------------------------------------
                55  AGGATATCC TGCAAGGCT TCTGGATAC ACATTCACT GACTACAAC ATACACTGG
                    TCCTATAGG ACGTTCCGA AGACCTATG TGTAAGTGA CTGATGTTG TATGTGACC

                                19C7 Variable Heavy Gene
                    ----------------------------------------------------------
               109  GTGAAACAG AGCCATGGA AAGAGCCTT GAGTGGATT GGATATATT TATCCTTAC
                    CACTTTGTC TCGGTACCT TTCTCGGAA CTCACCTAA CCTATATAA ATAGGAATG

                                19C7 Variable Heavy Gene
                    ----------------------------------------------------------
               163  AATGGTATT ACTGGCTAC AACCAGAAA TTCAAGAGC AAGGCCACA TTGACTGTA
                    TTACCATAA TGACCGATG TTGGTCTTT AAGTTCTCG TTCCGGTGT AACTGACAT

                                19C7 Variable Heavy Gene
                    ----------------------------------------------------------
               217  GACAGTTCC TCCAATACA GCCTACATG GACCTCCGC AGCCTGACA TCTGAGGAC
                    CTGTCAAGG AGGTTATGT CGGATGTAC CTGGAGGCG TCGGACTGT AGACTCCTG

                                19C7 Variable Heavy Gene
                    ----------------------------------------------------------
               271  TCTGCAGTC TATTTTTGT GCTAGAGAC GCTTATGAT TACGACTGG TTGGCTTAC
                    AGACGTCAG ATAAAAACA CGATCTCTG CGAATACTA ATGCTGACC AACCGAATG

                        19C7 Variable Heavy Gene
                    ------------------------------------ Linker ----------------
               325  TGGGGCCAA GGGACTCTG GTCACTGTC TCTGCAGGT CCCGCCAAG GAGTTGACG
                    ACCCCGGTT CCCTGAGAC CAGTGACAG AGACGTCCA GGGCGGTTC CTCAACTGC

                                                  19C7 Variable Light Gene
                        Linker                  ---------------------------------
                    --------------------------
               379  CCCCTGAAG GAGGCGAAG GTCTCTGAC ATCTTGCTG ACTCAGTCT CCAGTCATC
                    GGGGACTTC CTCCGCTTC CAGAGACTG TAGAACGAC TGAGTCAGA GGTCAGTAG
```

FIG.2A

19C7 Variable Light Gene

```
433  CTGTCTGTG AGTCCAGGA GAAAGAGTC AGTTTCTCC TGCAGGGCC AGTCAGAGC
     GACAGACAC TCAGGTCCT CTTTCTCAG TCAAAGAGG ACGTCCCGG TCAGTCTCG
```

19C7 Variable Light Gene

```
487  ATTGGCACA AACATATAT TGGTATCAG CAAAGAACA AATGGTTCT CCAAGGCTT
     TAACCGTGT TTGTATATA ACCATAGTC GTTTCTTGT TTACCAAGA GGTTCCGAA
```

19C7 Variable Light Gene

```
541  CTCATAAAG TATGCTTCT GAGTCTATC TCTGGGATC CCTTCCAGG TTTAGTGGC
     GAGTATTTC ATACGAAGA CTCAGATAG AGACCCTAG GGAAGGTCC AAATCACCG
```

19C7 Variable Light Gene

```
595  AGTGGGTCA GGGACAGAT TTTACTCTT AGCATCAAC AGTGTGGAG TCTGAAGAT
     TCACCCAGT CCCTGTCTA AAATGAGAA TCGTAGTTG TCACACCTC AGACTTCTA
```

19C7 Variable Light Gene

```
649  ATTGCTGAT TATTACTGT CAACAAAGT AATAACTGG CCATACACG TTCGGAGGG
     TAACGACTA ATAATGACA GTTGTTTCA TTATTGACC GGTATGTGC AAGCCTCCC
```

19C7 Variable Light Gene

```
703  GGGACCAAG CTGGAAATA AAACGG
     CCCTGGTTC GACCTTTAT TTTGCC
```

FIG.2B

| y=ml*exp(−m2*M0)+m3 | | |
|---|---|---|
| | Value | Error |
| m1 | 77.011 | 9.9361 |
| m2 | 0.0068528 | 0.0022053 |
| m3 | 183.38 | 4.2374 |
| Chisq | 431.53 | NA |
| R | 0.96172 | NA |

Primers used for library construction

| Name | Location | Sequence | |
|---|---|---|---|
| tpVHfor | pYD41 19C7VH5' | gaattcgcggcccagccggccatggccgaggtccagcttca gcagtca | SEQ ID NO: 1 |
| tpVHrev | pYD41 19C7 VH3' linker 40 | cttcaggggcgtcaactccttggcgggacctgcagagacagt gac | SEQ ID NO: 2 |
| tpVLfor | pYD41 19C7L5' linker 40 | ttgacgcccctgaaggaggcgaaggtctctgacatcttgctga ct | SEQ ID NO: 3 |
| tpVLrev | pYD41 19C7VL3'rev | gaagggccctctagactcgagggcggccgcccgttttatttcc ag | SEQ ID NO: 4 |
| 19H1spfor | pYD41 19C7 CDRH1 | gaaacctggggcctcagtgaggatatcctgcaaggcttctg **gatacacattcactgactacaacatacac**tgggt gaaacagagccatgga | SEQ ID NO: 5 |
| 19HF1rev | pYD41 19C7 VH FR1 | agaagccttgcaggatatcctcactgaggc | SEQ ID NO: 6 |
| pYD1AGAfor | pYD41 AGA2 for | agtaacgtttgtc ı | SEQ ID NO: 7 |
| | | | SEQ ID NO: 8 |
| | | ɩaggctctttccatggct | SEQ ID NO: 9 |
| 19H3spfor | pYD41 19C7 CDRH3 | catctgaggactctgcagtctatttttgtgctaga**gacgctta tgattacgactggttggcttac**tggggccaagggact ctggtcactgtc | SEQ ID NO: 10 |

FIG.8A

| | | | |
|---|---|---|---|
| 19HF3rev | pYD41 19C7 VH FR3 | tctagcacaaaaatagactgcagagtcctc | SEQ ID NO: 11 |
| 19L1spfor | pYD41 19C7 CDRL1 | ctgtgagtccaggagaaagagtcagtttctcctgc**agggc cagtcagagcattggcacaaacatatat**ttggtatc agcaaagaacaaatggttct | SEQ ID NO: 12 |
| 19LF1rev | pYD41 19C7 VL FR1 | gcaggagaaactgactctttctcctggact | SEQ ID NO: 13 |
| 19L2spfor | pYD41 19C7 CDRL2 | aaagaacaaatggttctccaaggcttctcataaag**tatgctt ctgagtctatctct**gggatcccttccaggtttagtggcagt | SEQ ID NO: 14 |
| 19LF2rev | pYD41 19C7 VL FR2 | ctttatgagaagccttggagaaccatt | SEQ ID NO: 15 |
| 19L3spfor | pYD41 19C7 CDRL3 | gtgtggagtctgaagatattgctgattattactgt**caacaaa gtaataactggccatacacg**ttcggagggggggacc aagctggaaata | SEQ ID NO: 16 |
| 19LF3rev | pYD41 19C7 VL FR3 | acagtaataatcagcaatatcttcaga | SEQ ID NO: 17 |
| pYD41rev2 | pYD41 post poly HIS | atagaaaaggatattacatgggaaaac | SEQ ID NO: 18 |
| 19FRH2 for | pYD41 19C7 FR H2 | tgggtgaaacagagccatggaaagagcctt | SEQ ID NO: 19 |
| 19FRH3 for | pYD41 19C7 FR H2 | aaggccacattgactgtagacagtt | SEQ ID NO: 20 |
| 19FRL2 for | pYD41 19C7 FR L2 | tggtatcagcaaagaaca | SEQ ID NO: 21 |
| 19FRL3 for | pYD41 19C7 FR L3 | gggatcccttccaggtttagtggc | SEQ ID NO: 22 |

FIG.8B

Equilibrium Dissociation constant (KD)
as measured on scFv expressing yeast

| Clone Name | scFv KD (nM) |
|---|---|
| Tn I 19C7 WT | 1.7 |
| TnI 19C7 AM1 | 0.36 |
| TnI 19C7 AM2 | 0.38 |
| TnI 19C7 AM3 | 0.42 |
| TnI 19C7 AM4 | 0.36 |

FIG.9

Measurement ranking of mouse chimeric antibodies in EIA assay

| Clone Name | Ab50 | Ag50 |
|---|---|---|
| Tn I 19C7 WT | 25ng/mL | 0.73 |
| TnI 19C7 AM1 | 25ng/mL | 0.39 |
| TnI 19C7 AM2 | 25ng/mL | 1.15 |
| TnI 19C7 AM3 | 25ng/mL | 0.78 |
| TnI 19C7 AM4 | 8ng/mL | 1.58 |

FIG.10

Architect Results comparing TnI 19C7 wild type to TnI 19C7 AM1

| Tn I 19C7 WT | Mean RLU | X/A |
|---|---|---|
| CalA | 1132 | 1 |
| CalB | 11321 | 10 |
| CalC | 21656 | 19 |
| CalD | 63838 | 56 |
| CalE | 383234 | 339 |
| CalF | 1463399 | 1293 |

| Tn I 19C7 AM1 | Mean RLU | X/A |
|---|---|---|
| CalA | 1241 | 1 |
| CalB | 16282 | 14 |
| CalC | 29986 | 26 |
| CalD | 90633 | 80 |
| CalE | 540658 | 478 |
| CalF | 1974094 | 1744 |

FIG.11

Troponin I 19C7 AM1 VH Sequence

```
SEQ ID NO: 25      GluValGln LeuGlnGln SerGlyPro AspLeuVal LysProGly AlaSerVal
SEQ ID NO: 23    1 GAGGTCCAG CTTCAGCAG TCAGGACCT GACCTGGTG AAACCTGGG GCCTCAGTG
SEQ ID NO: 24      CTCCAGGTC GAAGTCGTC AGTCCTGGA CTGGACCAC TTTGGACCC CGGAGTCAC

                                                CDR H1
                                   ------------------------------
                   ArgIleSer CysLysAla SerGlyTyr ThrPheThr AspTyrAsn LeuHisTrp
                55 AGGATATCC TGCAAGGCT TCTGGATAC ACATTCACG GACTATAAC TTACACTGG
                   TCCTATAGG ACGTTCCGA AGACCTATG TGTAAGTGC CTGATATTG AATGTGACC

                                                          CDR H2
                                                     ---------------
                   ValLysGln SerHisGly LysSerLeu GluTrpIle GlyTyrIle TyrProTyr
               109 GTGAAACAG AGCCATGGA AAGAGCCTT GAGTGGATT GGATATATT TATCCTTAC
                   CACTTTGTC TCGGTACCT TTCTCGGAA CTCACCTAA CCTATATAA ATAGGAATG

                                 CDR H2
                   ---------------------------------------
                   AsnGlyIle ThrGlyTyr AsnGlnLys PheLysSer LysAlaThr LeuThrVal
               163 AATGGTATT ACTGGCTAC AACCAGAAA TTCAAGAGC AAGGCCACA TTGACTGTA
                   TTACCATAA TGACCGATG TTGGTCTTT AAGTTCTCG TTCCGGTGT AACTGACAT

                   AspSerSer SerAsnThr AlaTyrMet AspLeuArg SerLeuThr SerGluAsp
               217 GACAGTTCC TCCAATACA GCCTACATG GACCTCCGC AGCCTGACA TCTGAGGAC
                   CTGTCAAGG AGGTTATGT CGGATGTAC CTGGAGGCG TCGGACTGT AGACTCCTG

                                                     CDR H3
                                          -------------------------------
                   SerAlaVal TyrPheCys AlaArgAsp AlaTyrAsp TyrAspTyr LeuThrAsp
               271 TCTGCAGTC TATTTTTGT GCTAGAGAC GCTTATGAT TACGACTAT CTGACGGAC
                   AGACGTCAG ATAAAAACA CGATCTCTG CGAATACTA ATGCTGATA GACTGCCTG

                   TrpGlyGln GlyThrLeu ValThrVal SerAla
               325 TGGGGCCAA GGGACTCTG GTCACTGTC AGCGCT
                   ACCCCGGTT CCCTGAGAC CAGTGACAG TCGCGA
```

FIG.12A

Troponin I 19C7 AM1 VL Sequence

```
SEQ ID NO: 28      AspIleLeu LeuThrGln SerProVal IleLeuSer ValSerPro GlyGluArg
SEQ ID NO: 26    1 GACATCTTG CTGACTCAG TCTCCAGTC ATCCTGTCT GTGAGTCCA GGAGAAAGA
SEQ ID NO: 27      CTGTAGAAC GACTGAGTC AGAGGTCAG TAGGACAGA CACTCAGGT CCTCTTTCT

                                      CDR L1
                                 ------------------------------------
                   ValSerPhe SerCysArg ThrSerLys AsnValGly ThrAsnIle HisTrpTyr
55                 GTCAGTTTC TCCTGCAGG ACCAGTAAG AACGTTGGC ACAAACATT CATTGGTAT
                   CAGTCAAAG AGGACGTCC TGGTCATTC TTGCAACCG TGTTTGTAA GTAACCATA

                                                            CDR L2
                                                        ---------------
                   GlnGlnArg ThrAsnGly SerProArg LeuLeuIle LysTyrAla SerGluArg
109                CAGCAAAGA ACAAATGGT TCTCCAAGG CTTCTCATA AAGTATGCT TCAGAGCGT
                   GTCGTTTCT TGTTTACCA AGAGGTTCC GAAGAGTAT TTCATACGA AGTCTCGCA

                   CDR L2
                   ------
                   LeuProGly IleProSer ArgPheSer GlySerGly SerGlyThr AspPheThr
163                TTACCTGGG ATCCCTTCC AGGTTTAGT GGCAGTGGG TCAGGGACA GATTTTACT
                   AATGGACCC TAGGGAAGG TCCAAATCA CCGTCACCC AGTCCCTGT CTAAAATGA

                                                                      CDR L3
                                                                      ------
                   LeuSerIle AsnSerVal GluSerGlu AspIleAla AspTyrTyr CysGlnGln
217                CTTAGCATC AACAGTGTG GAGTCTGAA GATATTGCT GATTATTAC TGTCAACAA
                   GAATCGTAG TTGTCACAC CTCAGACTT CTATAACGA CTAATAATG ACAGTTGTT

                   CDR L3
                   -----------------------
                   SerAsnAsn TrpProTyr ThrPheGly GlyGlyThr LysLeuGlu IleLysArg
271                AGTAATAAC TGGCCATAC ACGTTCGGA GGGGGGACC AAGCTGGAA ATAAAACGG
                   TCATTATTG ACCGGTATG TGCAAGCCT CCCCCCTGG TTCGACCTT TATTTTGCC
```

FIG.12B

CDR Sequence Listing for TnI 19C7 AM1–AM4 antibody

| | CDR H1 | 26 | 27 | 28 | 29 | 30 | 31 | 32 | 33 | 34 | 35 |
|---|---|---|---|---|---|---|---|---|---|---|---|
| SEQ ID NO: 30 | 19C7 WT | G | Y | T | F | T | D | Y | N | I | H |
| SEQ ID NO: 31 | 19C7 AM1 | – | – | – | – | – | – | – | – | L | – |
| SEQ ID NO: 32 | 19C7 AM2 | – | – | – | – | – | – | – | – | L | – |
| SEQ ID NO: 33 | 19C7 AM3 | – | – | S | – | – | – | – | – | L | – |
| SEQ ID NO: 34 | 19C7 AM4 | – | – | – | – | – | – | – | – | – | – |

| | CDR H1 | 95 | 96 | 97 | 98 | 99 | 100 | 100? | 100? | 101 | 102 |
|---|---|---|---|---|---|---|---|---|---|---|---|
| SEQ ID NO: 35 | 19C7 WT | D | A | Y | D | Y | D | W | L | A | Y |
| SEQ ID NO: 36 | 19C7 AM1 | – | – | – | – | – | – | Y | – | T | D |
| SEQ ID NO: 37 | 19C7 AM2 | – | – | – | – | – | – | Y | – | T | D |
| SEQ ID NO: 38 | 19C7 AM3 | – | – | – | – | – | – | Y | – | T | D |
| SEQ ID NO: 39 | 19C7 AM4 | – | F | – | – | S | – | A | – | – | D |

| | CDR L1 | 24 | 25 | 26 | 27 | 28 | 29 | 30 | 31 | 32 | 33 | 34 |
|---|---|---|---|---|---|---|---|---|---|---|---|---|
| SEQ ID NO: 40 | 19C7 WT | R | A | S | Q | S | I | G | T | N | I | Y |
| SEQ ID NO: 41 | 19C7 AM1 | – | T | – | K | N | V | – | – | – | – | H |
| SEQ ID NO: 42 | 19C7 AM2 | – | T | – | K | N | V | – | – | – | – | H |
| SEQ ID NO: 43 | 19C7 AM3 | – | T | – | K | N | V | – | – | – | – | H |
| SEQ ID NO: 44 | 19C7 AM4 | – | – | – | – | – | – | – | – | – | – | – |

| | CDR L2 | 50 | 51 | 52 | 53 | 54 | 55 | 56 |
|---|---|---|---|---|---|---|---|---|
| SEQ ID NO: 45 | 19C7 WT | Y | A | S | E | S | I | S |
| SEQ ID NO: 46 | 19C7 AM1 | – | – | – | – | R | L | P |
| SEQ ID NO: 47 | 19C7 AM2 | – | G | T | – | R | V | F |
| SEQ ID NO: 48 | 19C7 AM3 | – | – | – | – | – | – | – |
| SEQ ID NO: 49 | 19C7 AM4 | – | – | – | – | – | – | – |

FIG. 13

ANTIBODIES TO TROPONIN I AND METHODS OF USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATION(S)*

*This is a reissue of U.S. patent application Ser. No. 12/391,937, filed on Feb. 24, 2009, now U.S. Pat. No. 8,030,026.*

BACKGROUND OF THE INVENTION

1. Field of the Invention

The subject invention relates to antibodies to troponin I as well as methods of use thereof.

2. Background Information

Troponin I is a muscle protein which may be used in the determination of myocardial damage subsequent to or during, for example, a myocardial infarction. In particular, troponin I is one of three subunits of the troponin complex which is located on the thin filament of the muscle contractile apparatus. This complex has a primary role in controlling the process of muscle contraction. The other two subunits (i.e., T and C) are also immobilized on the thin myofilaments with troponin I in cardiac as well as skeletal muscle tissue.

Assays have been described which measure cardiac troponin I in human serum. For example, a radioassay has been used for this purpose (Cummins et al., Am Heart Journal 113:1333-1344 (1987). However, the assay utilized polyclonal antibodies having significant cross-reactivity to skeletal forms of troponin I. Further, a sandwich assay has been utilized which uses two different monoclonal antibodies (Bodar et al., Clinical Chemistry 38:2203-2214 (1992); see also U.S. Pat. No. 7,285,418). Unfortunately, such assays have a very high degree of imprecision. Thus, the need certainly exists for immunoassays that are highly specific for and sensitive to troponin I. These immunoassays must also utilize antibodies which do not possess cross-reactivity to troponin I found in skeletal tissue. In particular, such immunoassays are needed so that appropriate therapy can be utilized by the treating physician thereby giving the affected patient the best possible prognosis.

All patents and publications referred to herein are hereby incorporated in their entirety by reference.

SUMMARY OF THE INVENTION

The present invention pertains to binding proteins, particularly antibodies, capable of binding to cardiac troponin I. In particular, these antibodies bind to one or more epitopes of troponin I. Further, the present invention also provides methods of producing and using these binding proteins or portions thereof, for example, in diagnostic assays.

In particular, the present invention encompasses a Chinese Hamster Ovary (CHO) cell line, referred to as TnI 19C7 AM1 hG1 CHO 204, designated by American Type Culture Collection (ATCC) deposit number PTA-9816 as well as the recombinant antibody produced by this cell line.

Additionally, the present invention includes an isolated binding protein comprising an antigen-binding domain which binds to Troponin I, said antigen-binding domain comprising at least one complementarity determining region (CDR) comprising an amino acid sequence selected from the group consisting of: GYTFTDYNLH (SEQ ID NO:52), YIYPYNGITGYNQKFKS (SEQ ID NO:53), DAYDYDLTD (SEQ ID NO:54), RTSKNVGTNIH (SEQ ID NO:55), YASERLP (SEQ ID NO:56) and QQSNNWPYT (SEQ ID NO:57). The binding protein of the present invention may include, for example, at least 3 of these CDRs. Further, this binding protein may also comprise a human acceptor framework or scaffold. This binding protein may be selected from the group consisting of, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a functionally active epitope-binding fragment of any one of these entities.

The present invention also encompasses an isolated nucleic acid molecule encoding a binding protein, wherein the amino acid sequence of the variable heavy chain of the binding protein has at least 70% identity to SEQ ID NO.: 25 (see FIG. 12). This molecule may also comprise a variable light chain having at least 70% identity to SEQ ID NO.: 28 (see FIG. 12).

Furthermore, the present invention includes an isolated nucleic acid molecule encoding a binding protein, wherein the amino acid sequence of the variable heavy chain of said binding protein is SEQ ID NO.:25.

Additionally, the present invention includes an isolated nucleic acid molecule encoding a binding protein, wherein the amino acid sequence of the variable light chain of said binding protein is SEQ ID NO.: 28. The molecule may further comprise an isolated nucleic acid molecule encoding a variable heavy chain, wherein the amino acid sequence of the heavy chain is SEQ ID NO.: 25.

The present invention also includes a vector comprising one or more of the nucleic acid molecules described above, attached to a regulatory element (e.g., a promoter) as well as a host cell comprising this vector.

Moreover, the present invention includes a method of producing any of the binding proteins described above, capable of binding to Troponin I, which method comprises culturing the host cell, described above, for a time and under conditions sufficient to produce the binding protein of interest. The invention also includes the binding protein produced by this method.

Furthermore, the present invention encompasses a pharmaceutical composition comprising any one or more of the binding proteins described above and a pharmaceutically acceptable carrier.

Also, the present invention includes a method of detecting Troponin I antigen in a test sample. This method comprises the steps of: contacting the test sample with an antibody which binds to Troponin I and comprises SEQ ID NO:25 for a time and under conditions sufficient for the formation of antibody/antigen complexes; and detecting presence of the complexes, presence of the complexes indicating presence of Troponin I antigen in said test sample. The antibody may further comprise SEQ ID NO:28. The antibody may be produced by a Chinese Hamster Ovary cell line having ATCC deposit designation PTA-9816.

The present invention also includes a method of detecting Troponin I antigen in a test sample comprising the steps of: contacting the test sample with a first antibody which binds to Troponin I and comprises SEQ ID NO:25 for a time and under conditions sufficient for the formation of first antibody/antigen complexes; adding a conjugate to the first antibody/antigen complexes, wherein said conjugate comprises a second antibody attached to a signal generating compound capable of generating a detectable signal, for a time and under conditions sufficient to form first antibody/antigen/second antibody complexes; and detecting presence of a signal generating by the signal generating compound, presence of the signal indicating presence of Troponin I antigen in said test sample. The first antibody may further comprise SEQ ID NO:28 and may be produced by a Chinese Hamster Ovary cell line having ATCC deposit designation PTA-9816.

Also, the present invention includes a method of detecting Troponin I antigen in a test sample comprising the steps of contacting Troponin I antigen with an antibody to Troponin I for a time and under conditions sufficient to form Troponin I antigen/antibody complexes, wherein the antibody comprises SEQ ID NO:25 and is labeled with a signal-generating compound capable of generating a detectable signal; adding the test sample to said Troponin I antigen/antibody complexes for a time and under conditions sufficient to form Troponin I antigen/antibody/Troponin I test sample antigen complexes; and detecting presence of a signal generating by the signal generating compound, presence of the signal indicating presence of Troponin I antigen in the test sample. Again, the antibody may further comprise SEQ ID NO:28 and may be produced by a Chinese Hamster Ovary cell line having ATCC deposit designation PTA-9816.

The present invention also encompasses another method of detecting Troponin I antigen in a test sample. This method comprises the steps of: contacting the test sample with 1) a Troponin I reference antigen, wherein the antigen is attached to a signal generating compound capable of generating a detectable signal and 2) an antibody to Troponin I antigen wherein the antibody comprises SEQ ID NO:25, for a time and under conditions sufficient to form Troponin I reference antigen/antibody complexes; and detecting a signal generated by the signal generating compound, wherein the amount of Troponin I antigen detected in the test sample is inversely proportional to the amount of Troponin I reference antigen bound to the antibody. Again, the antibody may further comprise SEQ ID NO:28 and may be produced by a Chinese Hamster Ovary cell line having ATCC deposit designation PTA-9816.

In addition, the present invention includes pharmaceutical composition comprising any one or more of the binding proteins described above and a pharmaceutically acceptable carrier.

The present invention also encompasses a method of diagnosing acute coronary syndrome or myocardial infarction in a patient suspected of having one of these conditions. This method comprises the steps of: isolating a biological sample from the patient; contacting the biological sample with an antibody which binds to Troponin I and comprises SEQ ID NO:25, for a time and under conditions sufficient for formation of Troponin I antigen/antibody complexes; detecting presence of the Troponin I antigen/antibody complexes; dissociating the Troponin I antigen present in the complexes from the antibody present in said complexes; and measuring the amount of dissociated Troponin I antigen, wherein an amount of Troponin I antigen greater than approximately 1-5 times the Troponin I value of the $99^{th}$ percentile of a normal population indicates a diagnosis of acute coronary syndrome or myocardial infarction in the patient.

The present invention includes an additional method method of diagnosing acute coronary syndrome or myocardial infarction in a patient suspected of having one of these conditions. This method comprises the steps of: isolating a biological sample from the patient; contacting the biological sample with a first antibody which binds to Troponin I and comprises SEQ ID NO:25, for a time and under conditions sufficient for the formation of Troponin I antigen/antibody complexes; adding a conjugate to the resulting Troponin I antigen/antibody complexes for a time and under conditions sufficient to allow the conjugate to bind to the bound Troponin I antigen, wherein the conjugate comprises a second antibody attached to a signal generating compound capable of generating a detectable signal; detecting the presence of Troponin I antigen which may be present in said biological sample by detecting a signal generated by said signal generating compound; and measuring the amount of Troponin I antigen present in the test sample by measuring the intensity of the signal, an amount of Troponin I antigen greater than approximately 1-5 times the value of the $99^{th}$ percentile of a normal population indicating a diagnosis of acute coronary syndrome or myocardial infarction in the patient.

The present invention also includes a kit comprising any one or more of the monoclonal antibodies or binding proteins described above and, if needed, instructions describing the manner in which to use this kit.

Additionally, the present invention includes an isolated binding protein which comprises an antigen-binding domain, wherein the antigen-binding domain comprises at least one CDR comprising an amino acid sequence selected from the group consisting of:

CDR-VH1. $X_1$-$X_2$-$X_3$-$X_4$-$X_5$-$X_6$-$X_7$-$X_8$-$X_9$-$X_{10}$ (SEQ ID NO:63), wherein:

$X_1$ is G;
$X_2$ is Y;
$X_3$ is T or S;
$X_4$ is F;
$X_5$ is T;
$X_6$ is D;
$X_7$ is Y;
$X_8$ is N;
$X_9$ is I or L; and
$X_{10}$ is H.

CDR-VH2. $X_1X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO:64), wherein:

$X_1$ is Y;
$X_2$ is I;
$X_3$ is Y;
$X_4$ is P;
$X_5$ is Y;
$X_6$ is N;
$X_7$ is G;
$X_8$ IS I;
$X_9$ is T;
$X_{10}$ is G;
$X_{11}$ is Y;
$X_{12}$ is N;
$X_{13}$ is Q;
$X_{14}$ is K;
$X_{15}$ is F;
$X_{16}$ is K; and
$X_{17}$ is S.

CDR-VH3. $X_1$-$X_2$-$X_3$-$X_4$-$X_5$-$X_6$-$X_7$-$X_8$-$X_9$-$X_{10}$ (SEQ ID NO:65), wherein:

$X_1$ is D;
$X_2$ is A or F;
$X_3$ is Y;
$X_4$ is D;
$X_5$ is Y or S;
$X_6$ is D;
$X_7$ is W, Y or A;

$X_8$ is L;
$X_9$ is A or T; and
$X_{10}$ is Y or D.

CDR-VL1. $X_1$-$X_2$-$X_3$-$X_4$-$X_5$-$X_6$-$X_7$-$X_8$-$X_9$-$X_{10}$-$X_{11}$ (SEQ ID NO:66), wherein:
$X_1$ is R;
$X_2$ is A or T;
$X_3$ is S;
$X_4$ is Q or K;
$X_5$ is S or N;
$X_6$ is I or V;
$X_7$ is G;
$X_8$ is T;
$X_9$ is N;
$X_{10}$ is I; and
$X_{11}$ is Y or H.

CDR-VL2. $X_1$-$X_2$-$X_3$-$X_4$-$X_5$-$X_6$-$X_7$ (SEQ ID NO:67), wherein:
$X_1$ is Y;
$X_2$ is A or G;
$X_3$ is S or T;
$X_4$ is E;
$X_5$ is S or R;
$X_6$ is I, L or V; and
$X_7$ is S, P or F, and CDR-VL3. $X_1$-$X_2$-$X_3$-$X_4$-$X_5$-$X_6$-$X_7$-$X_8$-$X_9$ (SEQ ID NO:68), wherein:
$X_1$ is Q;
$X_2$ is Q;
$X_3$ is S;
$X_4$ is N;
$X_5$ is N;
$X_6$ is W;
$X_2$ is P;
$X_8$ is Y; and
$X_9$ is T.

BRIEF DESCRIPTION OF THE FIGURES

FIG. 2 is the nucleotide description (SEQ ID NO: 109 and SEQ ID NO: 110) of the wild-type TnI 19C7 single-chain variable fragment ("scFv").

FIG. 8 is a summary showing the PCR primers that were used to generate the scFv construct (tpVHfor through tpVL-rev), those used to generate the CDR spiked libraries (19H1spfor through pYD41rev2) and those used to generate the combination library (19FRH2for to 19FRL3) (see SEQ ID Nos:1-22). The bold and enlarged areas of the primers represent those regions in which a "70% wild-type, 30% other nucleotide mixture" was incorporated while the primers were being made. Such a "spiked" primer generated the diversity within the library.

FIG. 9 shows equilibrium dissociation constant (KD) measurements of selected TnI 19C7 scFv determined as described above in FIG. 5.

FIG. 10 shows the results of relative antibody affinity as measured as an antigen 50% (Ag50). Four TnI 19C7 clones were converted into mouse IgG2ak antibodies by cloning the variable domains onto the immunoglobulin constant domains. Antibodies were expressed in a transient HEK 294 cell system. The Ag50 is the concentration of scTnI-C at which is 50% of the maximum signal and represents the relative affinity ranking of the selected TnI 19C7 AM candidates. TnI 19C7 AM1 exemplifies the tightest relative affinity compared to the TnI 19C7 wild-type antibody.

FIG. 11 illustrates TnI 19C7 AM1's ability to bind to scTnI-C in an ARCHITECT® assay format (Abbott Laboratories, Abbott Park, Ill.). TnI 19C7 was labeled with acridinium and assayed for binding to scTnI-C using anti-TnI capture beads. (X=signal generated with given calibrator concentration of scTnI-C; X/A=ratio of calibrator X signal to calibrator A signal; RLU=Relative Light Units). TnI 19C7 AM1 exhibited better binding in this assay format for the range of calibrators compared to the wild-type TnI 19C7 antibody.

FIG. 12 illustrates the nucleotide (SEQ ID NO:23, SEQ ID NO:24 (complement), SEQ ID NO:26 and SEQ ID NO:27 (complement)) and encoded amino acid sequences of the heavy (SEQ ID NO:25) and light (SEQ ID NO:28) chains of monoclonal antibody TnI 19C7 AM1 and, in particular, of the complementarity determining regions (CDRs).

FIG. 13 illustrates the positions within the heavy and light chains of the TnI 19C7 CDRs that may be substituted with amino acids other than those shown in FIG. 12 (SEQ ID Nos: 30-49).

DETAILED DESCRIPTION OF THE INVENTION

Figure 1:
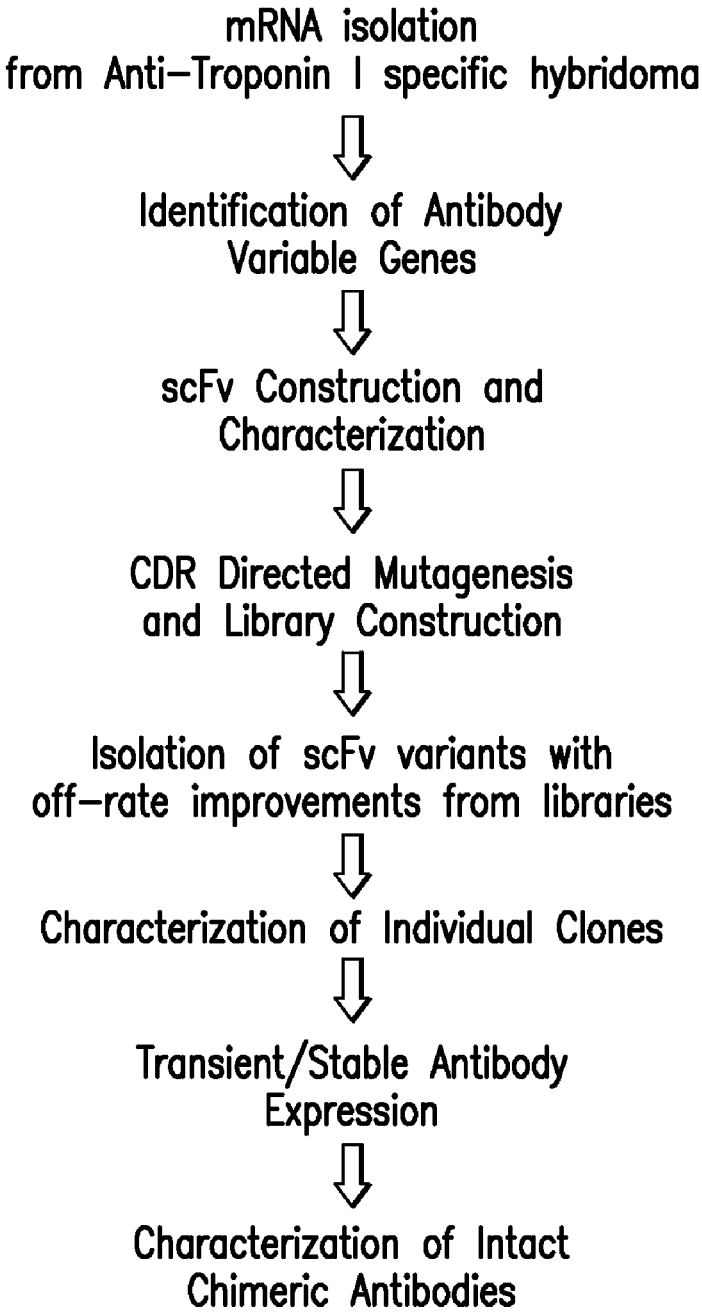
FIG. 1 is a flow chart showing the steps used to identify and create antibodies that have improved affinity for troponin I.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures-used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In order that the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The subject invention also includes isolated nucleotide sequences (or fragments thereof) encoding the variable light and heavy chains of the antibodies described herein as well as those nucleotide sequences (or fragments thereof) having sequences comprising, corresponding to, identical to, hybridizable to, or complementary to, at least about 70% (e.g., 70% 71%, 72%, 73%, 74%, 75%, 76%, 77%, 78% or 79%), preferably at least about 80% (e.g., 80%, 81%, 82%, 83%, 84%, 85%, 86%, 87%, 88% or 89%), and more preferably at least about 90% (e.g, 91%, 92%, 93%, 94%, 95%, 96%, 97%, 98%, 99% or 100%) identity to these encoding nucleotide sequences. (All integers (and portions thereof) between and including 70% and 100% are considered to be within the scope of the present invention with respect to percent identity.) Such sequences may be derived from any source (e.g., either isolated from a natural source, produced via a semi-synthetic route, or synthesized de novo). In particular, such sequences may be isolated or derived from sources other than described in the examples (e.g., bacteria, fungus, algae, mouse or human).

In addition to the nucleotide sequences described above, the present invention also includes amino acid sequences of the variable light and heavy chains of the antibodies described herein (or fragments of these amino acid sequences). Further, the present invention also includes amino acid sequences (or fragments thereof) comprising, corresponding to, identical to, or complementary to at least about 70% (e.g., 70%, 71%, 72%, 73%, 74%, 75%, 76%, 77%, 78% or 79%), preferably at least about 80% (e.g., 80% 81%, 82%, 83%, 84%, 85%, 86%, 87%, 88% or 89%), and more preferably at least about 90% identity (e.g., 90%, 91%, 92%, 93%, 94%, 95%, 96%, 97%, 98%, 99% or 100%), to the amino acid sequences of the proteins of the present invention. (Again, all integers (and portions thereof) between and including 70% and 100% (as recited in connection with the nucleotide sequence identities noted above) are also considered to be within the scope of the present invention with respect to percent identity.)

For purposes of the present invention, a "fragment" of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Winch, J. Mol. Biol. 48:443 (1970), by the method of Pearson & Lipmann, Proc. Natl. Acad. Sci. (USA) 85:2444 (1988) and by computer programs which implement the relevant algorithms (e.g., Crustal Macaw Pileup (Higgins et al., CABIOS. 5L151-153 (1989)), FASTDB (Intelligentsias), BLAST (National Center for Biomedical Information; Latches et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

"Biological activity" as used herein, refers to all inherent biological properties of an antibody against troponin I or troponin I. Such properties include, for example, the ability of the antibody to bind to troponin I and functionally-related antibodies described herein.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody entities are known in the art, non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG3, IgG4, IgA1 and IgA2) or subclass and may be from any species (e.g., mouse, human, chicken, rat, rabbit, sheep, shark and camelid).

The CDRs of the antibodies of the present invention are shown in Tables 1 and 2 below:

TABLE 1

CDRs OF HEAVY CHAIN FOR TnI 19C7 AM1

| SEQ ID NO. | Protein region | Sequence |
|---|---|---|
| 52 | CDR H1 | GYTFTDYNLH |
| 53 | CDR H2 | YIYPYNGITGYNQKFKS |
| 54 | CDR H3 | DAYDYDYLTD |

TABLE 2

CDRs OF LIGHT CHAIN FOR TnI 19C7 AM1

| SEQ ID NO. | Protein region | Sequence |
|---|---|---|
| 55 | CDR Ll | RTSKNVGTNIH |
| 56 | CDR L2 | YASERLP |
| 57 | CDR L3 | QQSNNWPYT |

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by one or more fragments of a full-length antibody. Such antibody embodiments may also be bispecific, dual specific, or multispecific, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., Intern. Appln. Public. No. WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed herein within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art, and examples are presented in Table 3.

TABLE 3

SEQUENCE OF HUMAN IgG HEAVY CHAIN CONSTANT DOMAIN AND LIGHT CHAIN CONSTANT DOMAIN

| Protein | Sequence Identifier | Sequence 1234567890123456789012345678901 2 |
|---|---|---|
| Ig gamma-1 constant region | SEQ ID NO.: 50 | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| Ig gamma-1 constant region mutant | SEQ ID NO.: 51 | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPEAAGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |

TABLE 3-continued

SEQUENCE OF HUMAN IgG HEAVY CHAIN CONSTANT DOMAIN AND LIGHT CHAIN CONSTANT DOMAIN

| Protein | Sequence Identifier | Sequence 1234567890123456789012345678901 2 |
|---|---|---|
| Ig Kappa constant region | SEQ ID NO.: 61 | TVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFN RGEC |
| Ig Lambda constant region | SEQ ID NO.: 62 | QPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPT ECS |

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds troponin I is substantially free of antibodies that specifically bind antigens other than troponin I). An isolated antibody that specifically binds troponin I may, however, have cross-reactivity to other antigens, such as troponin I molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described below), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann, S-A. and Green, L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species. The present invention encompasses chimeric antibodies having, for example, murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3. (In addition, for purposes of the present invention, the AbM definition as defined by Oxford Molecular's ABM antibody modeling software was used to define the CDR-H1 region from amino acids 26-35 for the heavy chain.)

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, such as AbM definitions, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat, AbM or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

In one embodiment of the invention, the murine heavy chain and light chain donor sequences are selected from the sequences described below:

TABLE 4

HEAVY CHAIN DONOR SEQUENCES FOR TnI 19C7 AM1

| SEQ ID No. | Sequence 123456789012345678901234567890 12 |
|---|---|
| 69 | EVTLRESGPALVKPTQTLTLTCTFSGFSLS |
| 70 | WIRQPPGKALEWLA |
| 71 | RLTISKDTSKNQVVLTMTNMDPVDTATYYCAR |
| 72 | WGQGTTVTVSS |
| 73 | EVTLKESGPVLVKPTETLTLTCTVSGFSLS |
| 74 | WIRQPPGKALEWLA |
| 75 | RLTISKDTSKSQVVLTMTNMDPVDTATYYCAR |
| 76 | WGQGTTVTVSS |
| 77 | EVQLVESGGGLVQPGGSLRLSCAASGFTFS |
| 78 | WVRQAPGKGLEWVG |
| 79 | RFTISRDDSKNSLYLQMNSLKTEDTAVYYCAR |
| 80 | WGQGTTVTVSS |
| 81 | EVQLVESGGGLVKPGGSLRLSCAASGFTFS |
| 82 | WVRQAPGKGLEWVS |
| 83 | RFTISRDNAKNSLYLQMNSLRAEDTAVYYCAR |
| 84 | WGQGTTVTVSS |

TABLE 4-continued

HEAVY CHAIN DONOR SEQUENCES FOR TnI 19C7 AM1

| SEQ ID No. | Sequence 123456789012345678901234567890 12 |
|---|---|
| 85 | EVQLVQSGAEVKKPGSSVKVSCKASGGTFS |
| 86 | WVRQAPGQGLEWMG |
| 87 | RVTITADKSTSTAYMELSSLRSEDTAVYYCAR |
| 88 | WGQGTTVTVSS |
| 89 | EVQLVQSGAEVKKPGASVKVS CKASGYTFT |
| 90 | WVRQAPGQGLEWMG |
| 91 | RVTMTTDTSTSTAYMELRSLRSDDTAVYYCAR |
| 92 | WGQGTTVTVSS |

TABLE 5

LIGHT CHAIN DONOR SEQUENCES FOR TnI 19C7 AM1

| SEQ ID No. | Sequence 123456789012345678901234567890 12 |
|---|---|
| 93 | DIVMTQSPDSLAVSLGERATINC |
| 94 | WYQQKPGQPPKLLIY |
| 95 | GVPDRFSGSGSGTDFTLTISSLQAEDVAVYYC |
| 96 | FGGGTKVEIKR |
| 97 | EIVMTQSPATLSVSPGERATLSC |
| 98 | WYQQKPGQAPRLLIY |
| 99 | GIPARFSGSGSGTEFTLTISSLQSEDFAVYYC |
| 100 | FGGGTKVEIKR |
| 101 | DIQMTQSPSSLSASVGDRVTITC |
| 102 | WYQQKPEKAPKSLIY |
| 103 | GVPSRFSGSGSGTDFTLTISSLQPEDFATYYC |
| 104 | FGGGTKVEIKR |
| 105 | DIQMTQSPSSVSASVGDRVTITC |
| 106 | WYQOKPGKAPKLLIY |
| 107 | GVPSRFSGSGSGTDFTLTISSLQPEDFATYYC |
| 108 | FGGGTKVEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, more preferably at least 90%, more preferably at least 95%, more preferably at least 98% and most preferably at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In other embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "activity" includes activities such as the binding specificity/affinity of an antibody for an antigen, for example, an anti-troponin I antibody that binds to troponin I.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$" or "$K_D$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. The terms "crystal", and "crystallized" as used herein, refer to an antibody, or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ed., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double-stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line E. coli; mammalian cell lines CHO, HEK 293 and COS; the insect cell line Sf9; and the fungal cell Saccharomyces cerevisiae or Picchia pastoris.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of troponin I). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of troponin I). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in International Application Publication No. WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, troponin I polypeptides, nucleic acids, carbohydrates, or any other molecules that bind to troponin I.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other mammalian or non-mammalian animals. Such substances include, but are not limited to, blood, serum, urine, synovial fluid, cells, organs, tissues (e.g., brain), bone marrow, lymph nodes, cerebrospinal fluid, and spleen.

Methods of Making Antibodies

Antibodies of the present invention may be made by any of a number of techniques known in the art. For example, antibodies can be prepared using a wide variety of techniques including the use of recombinant or phage display technologies, or a combination thereof. The term "monoclonal antibody" refers to an antibody that is derived from a single clone, including any eukaryotic, prokaryotic, or phage clone, and not the method by which it is produced.

In one embodiment, the present invention provides a method of generating recombinant antibodies (as well as antibodies produced by the method) comprising culturing a Chinese Hamster Ovary cell line secreting an antibody of the invention.

Further, fragments of the antibody of the present invention which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

Production of Anti-Troponin I Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al., U.S. Pat. No. 5,223,409; Kang et al., International Appln. Publication No. WO 92/18619; Dower et al., International Appln. Publication No. WO 91/17271; Winter et al., International Appln. Publication No. WO 92/20791; Markland et al., International Appln. Publication No. WO 92/15679; Breitling et al., International Appln. Publication No. WO 93/01288; McCafferty et al., PCT Publication No. WO 92/01047; Garrard et al., International Appln. Publication No. WO 92/09690; Fuchs et al. (1991), Bio/Technology 9:1370-1372; Hay et al., (1992) Hum Antibod Hybridomas 3:81-85; Huse et al. (1989), Science 246: 1275-1281; McCafferty et al., Nature (1990) 348:552-554; Griffiths et al. (1993) EMBO J 12:725-734; Hawkins et al., (1992) J Mol Biol 226:889-896; Clackson et al., (1991) Nature 352:624-628; Gram et al., (1992) PNAS 89:3576-3580; Garrad et al. (1991) Bio/Technology 9:1373-1377; Hoogenboom et al. (1991), Nuc Acid Res 19:4133-4137; and Barbas et al. (1991), PNAS 88:7978-7982, U.S. Patent Application Publication No. 20030186374, and International Application Publication No. WO 97/29131, the contents of each of which are incorporated herein by reference.

The recombinant antibody library may be from a subject immunized with troponin I, or a portion thereof Alternatively, the recombinant antibody library may be from a naive subject, i.e., one who has not been immunized with troponin I, such as a human antibody library from a human subject who has not been immunized with human troponin I. Antibodies of the invention are selected by screening the recombinant antibody library with the peptide comprising human troponin I to thereby select those antibodies that recognize troponin I. Methods for conducting such screening and selection are well known in the art, such as described in the references in the preceding paragraph. To select antibodies of the invention having particular binding affinities for troponin I, such as those that dissociate from human troponin I with a particular $k_{off}$ rate constant, the art-known method of surface plasmon resonance can be used to select antibodies having the desired $k_{off}$ rate constant.

In one aspect, the invention pertains to an isolated antibody, or an antigen-binding portion thereof, that binds human troponin I. In various embodiments, the antibody is a recombinant antibody.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup et al., U.S. Pat. No. 6,699,658 incorporated herein by reference.

Production of Recombinant Antibodies

As noted above, antibodies of the present invention may be produced by any number of techniques known in the art. For example, expression from host cells, wherein expression vector(s) encoding the heavy and light chains is (are) transfected into a host cell by standard techniques is the preferred method of producing the antibodies of the present invention. (The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.) Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr—CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr—CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Anti-Troponin Antibodies

The isolated anti-troponin I antibody CDR sequences described herein (see Tables 1 and 2) establish a novel family of troponin I binding proteins, isolated in accordance with this invention, and comprising polypeptides that include the CDR sequences listed in Tables 1 and 2 above. To generate and to select CDRs of the invention having preferred troponin I binding activity, standard methods known in the art for generating binding proteins of the present invention and assessing the binding characteristics thereof may be used, including but not limited to those specifically described herein.

Anti-Troponin I Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies, such as those of the present invention, are well known in the art. See e.g., Morrison, Science 229:1202 (1985); Oi et al., BioTechniques 4;214 (1986); Gillies et al., (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the antibodies described above with a human IgG1 constant region. In a specific embodiment, the chimeric antibody of the invention comprises a heavy chain variable region ($V_H$) comprising the amino acid sequence of SEQ ID NO:25 and a light chain variable region ($V_L$) comprising the amino acid sequence of SEQ ID NO:28.

Anti-Troponin I CDR Grafted Antibodies

CDR-grafted antibodies of the invention comprise heavy and light chain variable region sequences from a human antibody wherein one or more of the CDR regions of $V_H$ and/or $V_L$ are replaced with CDR sequences of the murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing chimeric antibodies are known in the art and discussed in detail in Example 2.2. (See also EP 239,400; Intern. Appln. Publication No. WO 91/09967; U.S. Pat. Nos. 5,225,539; 5,530,101; and 5,585,089), veneering or resurfacing (EP 592,106; EP 519,596; Padlan, Molecular Immunology 28(4/5): 489-498 (1991); Studnicka et al., Protein Engineering 7(6): 805-814 (1994); Roguska et al., PNAS 91:969-973 (1994)), and chain shuffling (U.S. Pat. No. 5,565,352).

Humanized Antibodies

Humanized antibodies are antibody molecules from non-human species antibody that bind the desired antigen having one or more complementarity determining regions (CDRs) from the non-human species and framework regions from a human immunoglobulin molecule Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska et al., PNAS 91:969-973 (1994); International Appln. Publication No. WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Production of Antibodies and Antibody-Producing Cell Lines

As noted above, preferably, antibodies of the present invention exhibit a high capacity to bind specifically to troponin I, e.g., as assessed by any one of several in vitro and in vivo assays known in the art (e.g., see examples below).

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter et al., U.S. Pat. Nos. 5,648,260 and 5,624,821). The Fc portion of an antibody mediates several important effector functions, for example, cytokine induction, ADCC, phagocytosis, complement dependent cytotoxicity (CDC) and half-life/clearance rate of antibody- and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement Clq, respectively. Neonatal Fc receptors (FcRn) are the critical components determining the circulating half-life of antibodies. In still another embodiment, at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably, the invention relates to crystals of whole anti-troponin I antibodies and fragments thereof as disclosed herein, and formulations and compositions comprising such crystals. In one embodiment the crystallized binding protein has a greater half-life in vivo than the soluble counterpart of the binding protein. In another embodiment, the binding protein-retains biological activity after crystallization.

Crystallized binding protein of the invention may be produced according methods known in the art and as disclosed in International Appln. Publication No. WO 02/072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, Biotechnol. Prog. 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. The creation of glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in International Appln. Publication No. WO 03/016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; International Appln. Publication Nos. WO 03/035835 and WO 99/5434280, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Patent Application Publication Nos. 20040018590 and 20020137134 and International Appln. Publication No. WO 05/100584 A2).

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

One aspect of the invention pertains to a DVD binding protein comprising binding proteins capable of binding to troponin I. Preferably, the DVD binding protein is capable of binding troponin I and a second target. The present invention also encompasses triple-variable domain (TVD) binding proteins in which the antibody is capable of binding troponin I as well as two additional targets (i.e., a second and third target).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein (e.g., antibody of interest) or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

Diagnostic Uses of Anti-Troponin I Antibodies

Given their ability to bind to troponin I, the anti-troponin I antibodies, or portions thereof, of the invention can be used to detect troponin I (e.g., in a biological sample such as serum, whole blood, CSF, brain tissue or plasma), using a conventional immunoassay competitive or non-competitive assay such as, for example, an enzyme linked immunosorbent assay (ELISA), a radioimmunoassay (RIA), an immunometric assay or tissue immunohistochemistry. The invention therefore provides a method for detecting troponin I in a biological sample comprising contacting a biological sample with an antibody, or antibody portion, of the invention and detecting either the antibody (or antibody portion) bound to troponin I or unbound antibody (or antibody portion), to thereby detect troponin I in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

As an alternative to labeling the antibody, troponin I can be assayed in biological fluids by a competition immunoassay utilizing recombinant troponin I standards labeled with a detectable substance and an unlabeled anti-troponin I antibody. In this assay, the biological sample, the labeled recombinant troponin I standards and the anti-troponin I antibody are combined, and the amount of labeled recombinant troponin I standard bound to the unlabeled antibody is determined. The amount of troponin I in the biological sample is inversely proportional to the amount of labeled recombinant troponin I standard bound to the anti-troponin I antibody.

In particular, in one embodiment of the present invention, one or more of the antibodies of the present invention are coated on a solid phase (or are in a liquid phase). The test or biological sample (e.g., serum, plasma, urine, etc.) is then contacted with the solid phase. If troponin I antigens are present in the sample, such antigens bind to the antibodies on the solid phase and are then detected by either a direct or indirect method. The direct method comprises simply detecting presence of the complex itself and thus presence of the antigens. It should be noted that one may use the full antibody or a fragment thereof in connection with the antibodies coated on the solid phase. (For purposes of the present invention, a "fragment" or "portion" of an antibody is defined as a subunit of the antibody which reacts in the same manner, functionally, as the full antibody with respect to binding properties.)

As mentioned above, in the indirect method, a conjugate is added to the bound antigen. The conjugate comprises a second antibody, which binds to the bound antigen, attached to a signal-generating compound or label. Should the second antibody bind to the bound antigen, the signal-generating compound generates a measurable signal. Such signal then indicates presence of the antigen (i.e., troponin I) in the test sample.

Examples of solid phases used in diagnostic immunoassays are porous and non-porous materials, latex particles, magnetic particles, microparticles (see U.S. Pat. No. 5,705,330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

As noted above, examples of biological fluids which may be tested by the above immunoassays include plasma, urine, whole blood, dried whole blood, serum, cerebrospinal fluid, saliva, tears, nasal washes or aqueous extracts of tissues and cells.

Additionally, it should also be noted that the initial capture antibody (for detecting troponin I antigens) used in the immunoassay may be covalently or non-covalently (e.g., ionic, hydrophobic, etc.) attached to the solid phase. Linking agents for covalent attachment are known in the art and may be part of the solid phase or derivatized to it prior to coating.

Further, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

Of course, any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AXSYM, IMX, PRISM, and Quantum II platforms, as well as other platforms.

Other assay formats which may be used for purposes of the present invention include, for example, a rapid test, a Western blot, as well as the use of paramagnetic particles in, for example, an ARCHITECT® assay (see Frank Quinn, The Immunoassay Handbook, Second edition, edited by David Wild, pages 363-367, 2001, herein incorporated in its entirety by reference). Such formats are known to those of ordinary skill in the art.

It should also be noted that the elements of the assays described above are particularly suitable for use in the form of a kit. The kit may also comprise one container such as a vial, bottle or strip. These kits may also contain vials or containers of other reagents needed for performing the assay, such as washing, processing and indicator reagents.

Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which troponin I activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and International Appln. Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; International Appln. Publication No. WO 99/15154; and International Appln. Publication No. WO 99/20253. Examples of polymers used in sustained release formulations include, but are not limited to, poly(2-hydroxy ethyl methacrylate), poly(methyl methacrylate), poly(acrylic acid), poly (ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, International Appln. Publication No. WO 91/05548, International Appln. Publication No. WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Proc. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

It should be understood that the antibodies of the invention or antigen binding portion thereof can be used alone or in combination with one or more additional agents, e.g., a therapeutic agent (for example, a small molecule or biologic), said additional agent being selected by the skilled artisan for its intended purpose. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limiting. The combinations, which are part of this invention, can be the antibodies of the present invention and at least one additional agent selected from the lists below. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Having now described the present invention in detail, the same will be more clearly understood by reference to the following examples, which are included for purposes of illustration only and are not intended to limit the scope of the present invention.

EXAMPLES

Example I

Generation and Isolation of 19C7

Identification of Immunoglobulin Genes

Messenger RNA was isolated from subcloned anti-TnI 19C7-144 hybridoma cells. (Hybridoma cell line TnI 19C7 is described in U.S. Patent Application Publication No. US2006/0018897.) TnI 19C7 mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and thus the immunoglobulin variable heavy and variable light chain genes were identified (see FIG. 2).

Cloning TnI 19C7 Variable Region Genes into pYD41 Vector

A yeast display system was used to express unmutated or wild-type anti-TnI proteins (described herein infra) and a library of anti-TnI proteins on the yeast surface as a fusion to the yeast protein AGA2. A yeast display vector called pYD (Invitrogen, Carlsbad, Calif.) was used as it allows for cloning of the anti-TnI gene at the C-terminus of the AGA2 gene, a yeast mating factor (See, Boder and Wittrup, Nature Biotechnology, 15:553-557 (June 1997)). Other critical features of the pYD vector include a galactose inducible promoter and an epitope tag, V5, on the C-terminus of the inserted anti-TnI gene (see FIG. 12).

The yeast display platform utilizes an antibody format known as the single-chain variable fragment. In the scFv format, the variable heavy domain is connected to the variable light domain through a flexible linker (variable heavy domain—Linker GPAKELTPLKEAKVS (SEQ ID NO:58)—variable light domain).

PCR single overlap extension (SOE) was used to combine the variable heavy (VH) and the variable light genes (VL) for the TnI 19C7 scFv construct (FIG. 2, and SEQ ID NOs:54 and 55). The TnI 19C7 scFv DNA was cloned into the yeast display vector pYD41 using vector restriction sites SfiI and XhoI. The pYD41-TnI 19C7scFv vector was transformed into DH5α E. coli. Plasmid DNA was then isolated from the E. coli and the TnI 19C7 scFv insert was sequenced to ensure the scFv was cloned in frame with the AGA2 protein.

The cloning site for the scFv into the yeast display vector pYD41 is in an ORF that includes the following genes: AGA2-tether linker 41-X press epitope tag-TnI 19C7 variable heavy chain-Linker 40-TnI 19C7 variable light chain-V5 epitope tag—Six His tag (SEQ ID NO: 29). In addition, the yeast strain EBY100 is a tryptophan auxotroph and the pYD41 vector encodes for tryptophan as the system's selectable marker.

Transformation into Saccharomyces cerevisiae Strain EBY100

Figure 3A:
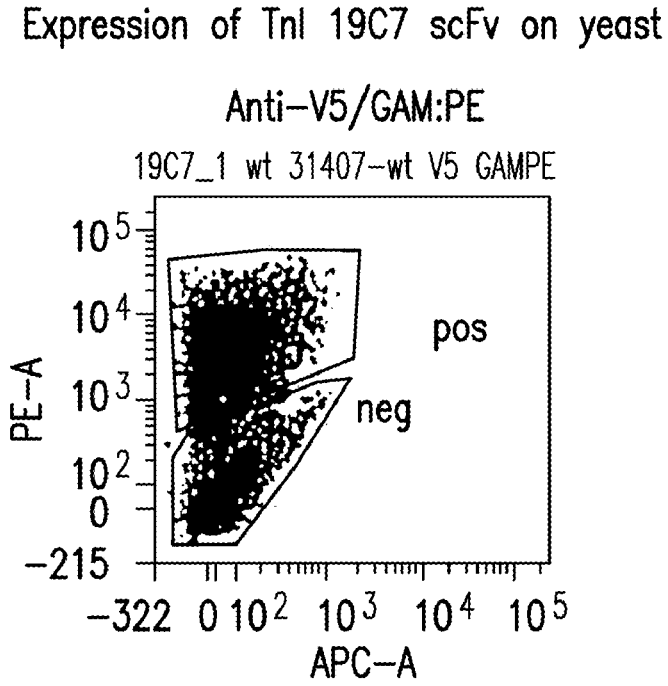
FIG. 3 shows that yeast expressing full-length TnI 19C7 single-chain variable fragment (scFv) bind to single chain troponin I (28-110aa)-linker-troponin C known as scTnI-C-2 (Spectral diagnostics, RP-3700). More specifically, this figure shows that TnI 19C7 scFv expressing yeast were incubated with scTnI-C-2 or anti-V5, followed by either anti-troponin mAb and goat anti mouse-phycoerythrin (GAM:PE) (FIG. 3B) or GAM:PE respectively (FIG. 3A). The flow cytometry histograms illustrate the full-length expression of TnI 19C7 scFv as detected by anti-V5 and the ability of TnI 19C7 scFv to bind to scTnI-C-2. PE-A units (abscissa). $10^2$, $10^3$, $10^4$, and $10^5$. Count units (ordinate): $10^2$, $10^3$, $10^4$, and $10^5$.
Figure 3B:
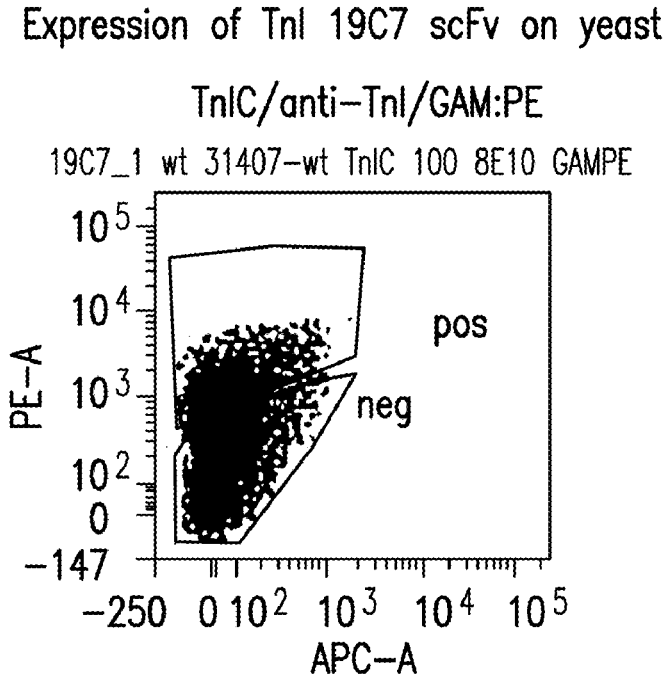

Yeast display plasmid, pYD41-TnI 19C7 scFv, was transformed into S. cerevisiae EBY100 using the Gietz and Schiestl Method (See Schiestl and Gietz, Current Genetics, 16(5-6):339-46 (December 1989)). Dilutions of the transformation reaction were plated on selective glucose plates (2% glucose (0.67% yeast nitrogen base, 0.105% HSM-trp-ura, 1.8% bacterial agar, 18.2% sorbitol, 0.86% $NaH_2PO_4$ $H_2O$, 1.02% $Na_2HPO_4$ $7H_2O$)) and incubated at 30° C. for 48-72 hours. Selective glucose media was inoculated with individual colonies and grown shaking at 30° C. for 16-20 hours. Protein expression was induced in colonies by transferring 0.5 OD600 of cells/ml (1e7 cells/0.50 D/ml) to selective galactose media. Colonies were shaken at 20° C. for 16-24 hours and then analyzed by the FACS Aria flow cytometer for binding to scTnI-C-2 and anti-V5. (It should be noted that scTnI-C-2 is a linked, single-chain TnI (28-110aa)-linker-TnC (1-160aa) from Spectral Diagnostics, Toronto, Canada. ScTnI-C-2 is abbreviated as "scTnI-C" for purposes of the present discussion.) For flow cytometry assays, yeast cells expressing TnI 19C7 scFv incubated with scTnI-C-2 or anti-V5 followed by either anti-troponin mAb and goat anti mouse-phycoerythrin (GAM:PE) (FIG. 3B) or GAM:PE respectively (FIG. 3A). The flow cytometry histograms illustrate the full-length expression of TnI 19C7 scFv as detected by anti-V5 and the ability of TnI 19C7 scFv to bind to scTnI-C-2.

Off-Rate Analysis for TnI 19C7 scFv and TnI 19C7 Variants on Yeast

Figure 4:
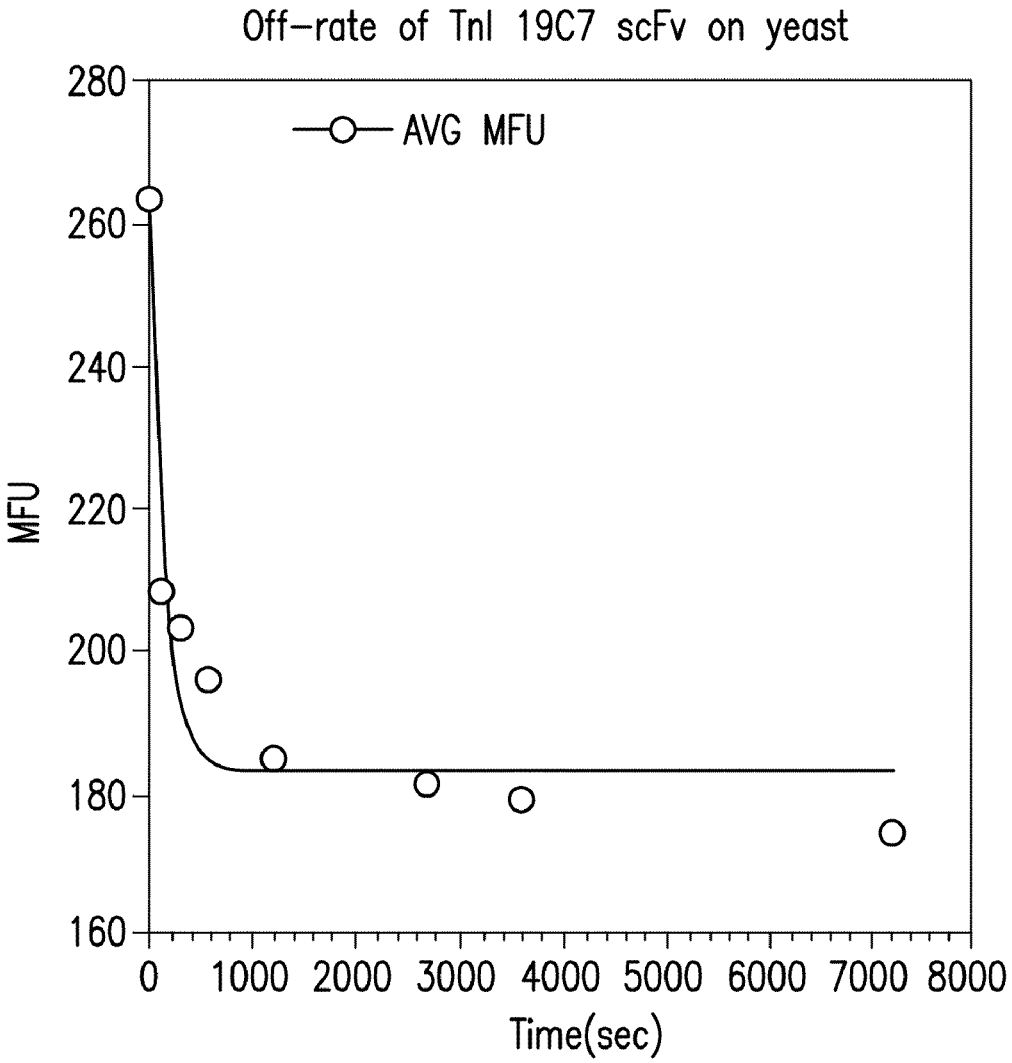
FIG. 4 shows the TnI 19C7 scFv off-rate measurement. More specifically, yeast expressing TnI 19C7 scFv were incubated with a saturating concentration of scTnI-C-2. Cells were washed twice and at each time point, cells were transferred to ice, washed and incubated with anti-TnI mAb. After 30 minutes, cells were washed again and incubated with goat anti-mouse phycoerythrin. Again after 30 minutes, cells were washed and analyzed on the flow cytometer. A first order decay equation was used to fit the individual time points where ml was the theoretical maximum mean fluorescence units ("MFU") at time 0, m2 was the off-rate ("koff"), m3 was the background MFU due to autofluorescence and M0, which is the time x (the x being the time that is being measured) was the time x that measurements are taken. The half-life ($t_{1/2}$) of TnI 19C7 scFv binding to TnI-C-2 was calculated using: $t_{1/2}=\ln 2/k_{off}$. Five times the half-life was the time used to sort the TnI 19C7 scFv CDR mutagenic libraries.

Off-rate measurements of TnI 19C7 scFv and TnI 19C7 variants on yeast were measured by incubating 0.05OD yeast ($1\times10^6$ cells) with 50 nM scTnI-C-2 for 30-60 minutes at room temperature. Cells were then washed twice with blocking buffer containing phosphate buffered saline pH 6.8 with 2% bovine serum albumin and 0.2% Standapol ES-1 (PBS/BSA/Standapol) and incubated at room temperature for varying amounts of time (0, 0.25 hr, 0.5 hr, 1 hr, 2 hr, 4.25 hr, 25.5 hr, 50 hr 75 hr and 144 hr (see FIG. 4). At each individual time point, yeast cells were transferred to ice to halt the reaction. Cells were then washed twice with blocking buffer and suspended in the next staining reagent, specifically, anti-TnI mAb 8E10 at 100 nM. Cells were incubated on ice for 30 minutes, washed twice and then incubated with goat anti mouse-phycoerythrin (GAM:PE). Finally, the cells were washed and analyzed on the FACS Aria flow cytometer. FIG. 4 shows the off-rate data plotted as mean fluorescence units ("MFU") versus time (in seconds). A first order decay equation was used to fit the data. The off-rate, m2 in the equation shown in FIG. 4, was fitted to 0.007 $sec^{-1}$. The TnI 19C7 scFv half-life ($t_{1/2}$) was approximately 8.5 min ($t_{1/2}$=ln 2/$k_{off}$).

An off-rate sorting strategy was used to identify off-rate improved TnI 19C7 variants from mutagenic libraries. Therefore, the TnI 19C7 scFv, unmutated or wildtype ("wt"), half-life was used to determine the appropriate time to sort the mutagenic libraries. TnI 19C7 mutagenic libraries were sorted approximately 9 min after washing cells free of scTnI-C-2 with the same assay conditions described for wt TnI 19C7 scFv.

Equilibrium Disassociation (KD) Analysis for TnI 19C7 scFv and TnI

Figure 5:
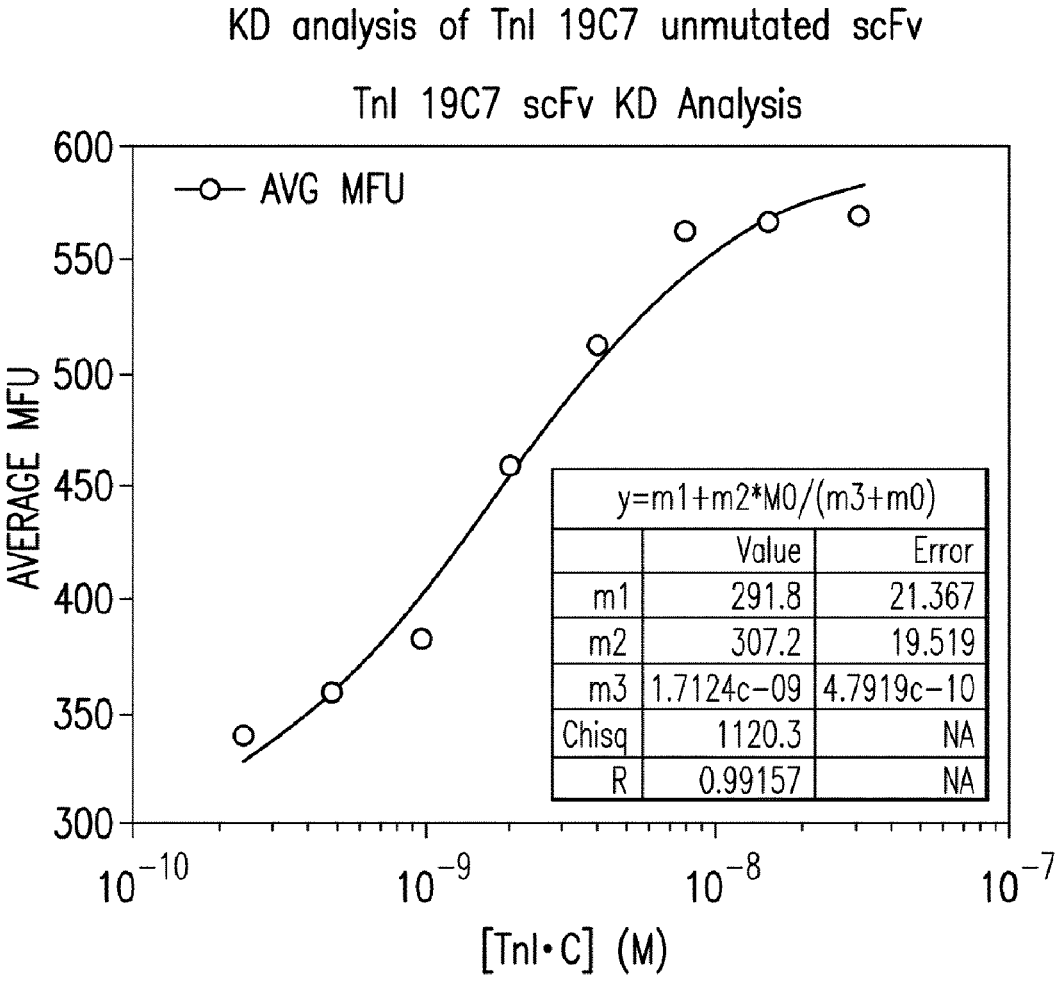
FIG. 5 shows the TnI 19C7 scFv equilibrium dissociation constant (KD) measurement. More specifically, yeast expressing TnI 19C7 scFv were incubated with varying concentrations of scTnI-C-2. Cells were washed twice with PBS pH6.8/2% BSA/0.02% Standapol ES-1 and incubated with anti-TnI mAb for 30 min Cells were washed again and incubated with goat anti-mouse phycoerythrin for 30 min. Finally, cells were washed and analyzed on the flow cytometer.
Figure 6:
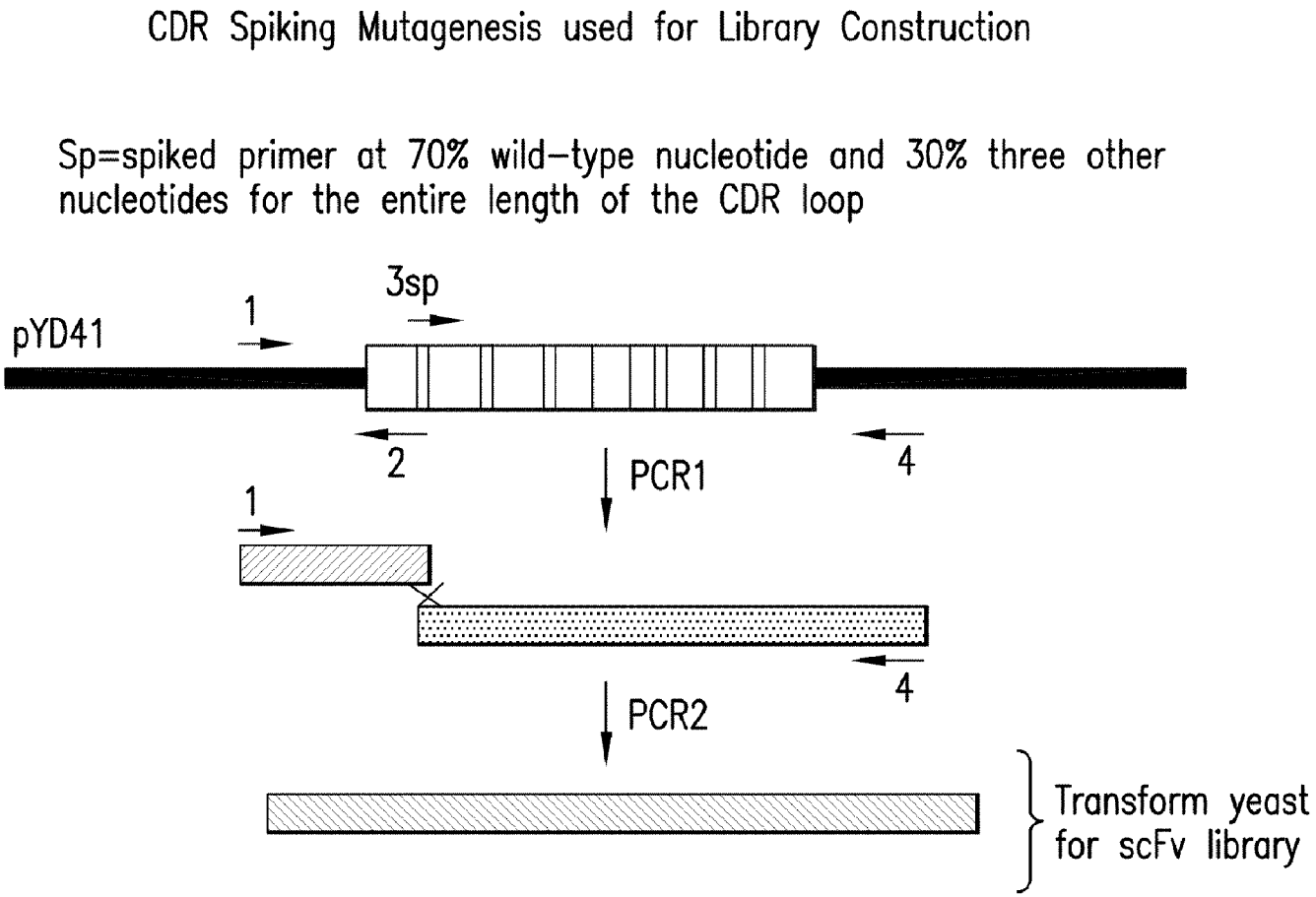
FIG. 6 is a schematic depiction that shows how degenerate oligonucleotides were designed so that primers are made such that for each CDR nucleotide residue 70% remains the wild-type residue and 30% a mix of the other three residues. Two PCR products are generated for each library a spiked (sp) PCR product and a non-spiked PCR product. The spiked and non-spiked PCR products are combined to generate an intact CDR mutagenized scFv library.

KD measurements of TnI 19C7 scFv and TnI 19C7 variants on yeast were measured by incubating 0.05 OD yeast ($1\times10^6$ cells) with varying concentrations of scTnI-C-2 for 45-60 minutes at room temperature. Blocking buffer containing phosphate buffered saline pH 6.8 with 2% bovine serum albumin and 0.2% Standapol ES-1 (PBS/BSA/Standapol) was used for washes and reagent dilutions. Cells were then washed twice and incubated for 30 min with anti-TnI mAb, 8E10. Cells were washed again and incubated with goat anti-mouse phycoerythrin for 30 min. Finally, cells were washed and analyzed on the FACS Aria flow cytometer (see FIG. 5). FIG. 5 shows the KD data plotted as normalized mean fluorescence units ("MFU") versus concentration scTn-I-C-2 (in Molarity). The antibody-normalized, antigen-binding mean fluorescence intensity was plotted against antigen concentration and a non-linear least squares fit (y=m1+m2*m0/(m3+m0)) was used to determine $K_D$.

Generation of TnI 19C7 Spiked CDR Libraries

Mutagenesis was directed to the three heavy and three light chain complementary determining regions (CDR) of antibody TnI 19C7 since these loops are the major antigen contact sites. CDR loop lengths and numbering were defined using Kabat and Oxford's Molecular AbM modeling nomenclature. Individual libraries were composed such that random mutations are incorporated at each amino acid position of the CDR for a single library. A total of six libraries were generated corresponding to one library per each CDR.

Figure 7:
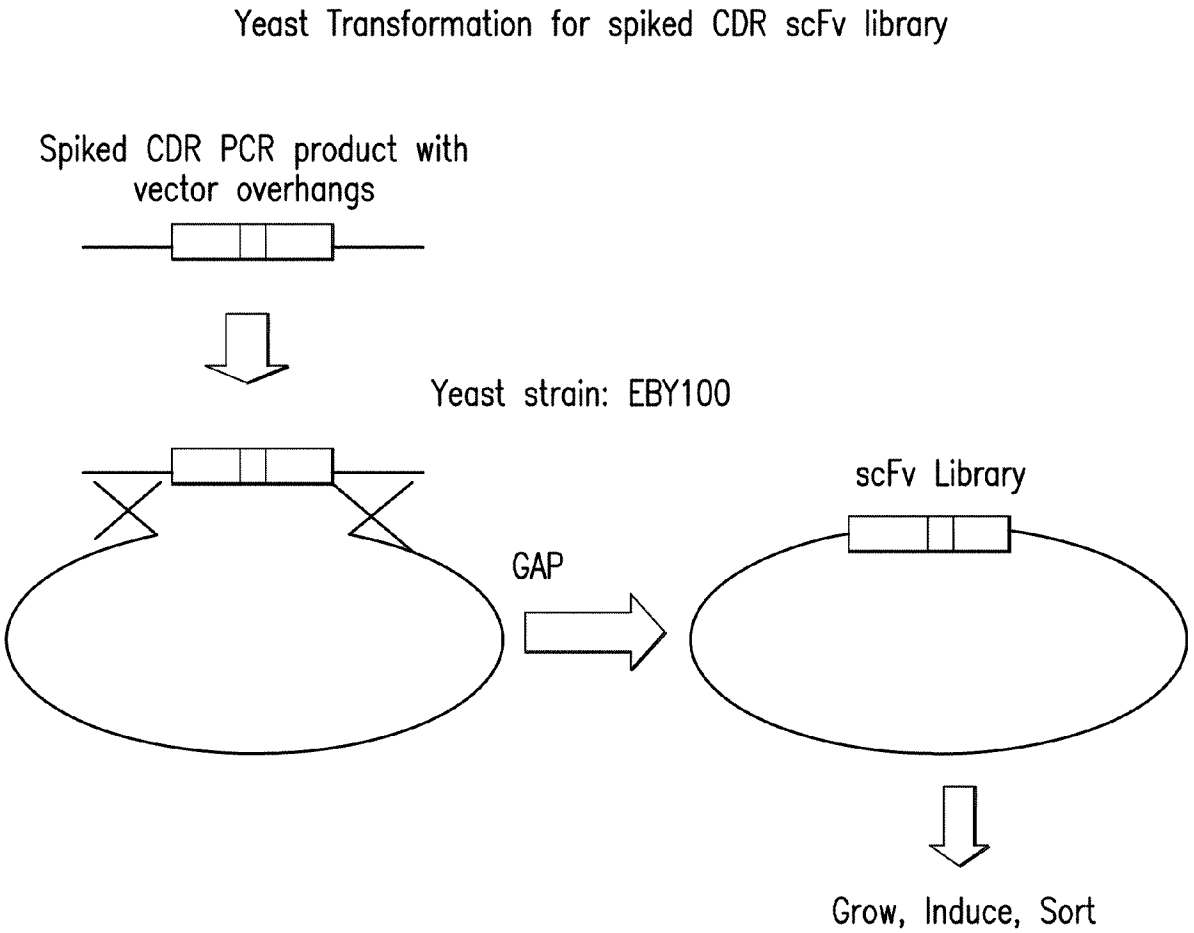
FIG. 7 is a schematic depiction that shows how the TnI 19C7 scFv library was constructed using yeast homologous recombination. More specifically, the spiked CDR PCR product and the excised yeast display vector were transformed into S. cerevisiae strain EBY100. Transformed clones were selected in tryptophan deficient glucose media.

Libraries were generated by combining SfiI/XhoI digested. pYD41 vector and PCR products with chemically competent EBY100 yeast (see FIG. 7). Two PCR products were generated for each CDR library to allow for PCR sorting and homologous recombination into yeast. One PCR product used a primer that was designed, such that for the entire length of the CDR, a 70% wild type to 30% other nucleotide ratio was used in the primer synthesis. This product was called the spiked (sp) product (see FIG. 7). The second PCR product was designed to include the remaining portion of the scFv gene. The two PCR products were combined and used to generate a single-chain variable fragment or a scFv product. Digested vector (1 ug) and the scFv PCR products (5 ug) were combined with EBY100 yeast (5.2e8-6.4e8 cells) and transformed using electroporation. The scFv PCR product and the pYD41 digested vector cyclize during transformation due to homologous recombination facilitated by the nucleotide overlap and the mechanism of yeast endogenous gap repair. Libraries were grown at 30° C. for 48-72 hours in selective glucose media and passed again in selective glucose media prior to induction of protein expression for library sorting.

TnI 19C7 Mutagenic CDR Libraries

TnI 19C7 libraries were sorted based on an off-rate sorting strategy. TnI 19C7 CDR mutagenic libraries were induced in galactose expression media at 20° C. for 18-24 hours. TnI 19C7 scFv and TnI 19C7 libraries on yeast were incubated with 25-50 nM scTnI-C-2 for 10-15 minutes at room temperature. Cells were then washed twice with blocking buffer containing phosphate buffered saline pH 6.8 with 2% bovine serum albumin and 0.2% Standapol ES-1 (PBS/BSA/Standapol) and incubated at room temperature for 8 min. Yeast cells were transferred to ice to halt the reaction. Cells were then washed twice with blocking buffer and suspended in the next staining reagent, specifically, anti-TnI mAb 8E10 at 100 nM and anti-V5 at 1.5-2 ug/ml. Cells were incubated on ice for 30 minutes, washed twice and then incubated with 1:200 goat anti mouseIgG2a-phycoerythrin (GAMIgG2a:PE) and with 1:200 dilution goat anti mouseIgG1-Alexa Fluor488 (GAMIgG1:488). Finally, the cells were washed, analyzed, and sorted on the FACS Aria flow cytometer. Sort gates were set based on unmutated TnI 19C7 binding at 8-9 min with a gate set to sort full-length TnI binding clones. Each sort collected the top 0.1-0.5% of the TnI binding population. Sorted cells were grown in selective glucose media and grown 18-24 hours at 30° C. Sort 1 cells were induced and sorting was repeated for two or three additional rounds.

After the last sort, sorted cells were plated onto selective glucose plates and placed at 30° C. for 72 hours. Individual yeast colonies from these libraries were inoculated in selective glucose media, cryopreserved and induced in selective galactose media. Individual colonies were then characterized and ranked in an off-rate assay. TnI 19C7 AM4 was isolated and identified from this sorting output.

Generation and Analysis of TnI 19C7 Combinatorial Mutant Clones

Clones that were characterized for off-rate from each master CDR library or the total master CDR library output were used to construct scFv genes containing different pairings of the individual mutations. This approach enabled determination of whether the binding properties were further enhanced upon combining individual mutations. Combinatorial clones containing various mutations in each CDR region were constructed by PCR amplification and combined using routine techniques known to those skilled in the art. Combinatorial mutant libraries were transformed into yeast as described above and sorted two times using off-rate and KD selection pressures. For KD selection, 100 pM (round 1) and 50 pM (round 2) scTnI-C were used in the KD experiment as described above (FIG. 5). For off-rate sorting, sorting was conducted as described above with incubation times following washing away of antigen of 3 hr 40 min (round 1) and 4 hrs 25 min (round 2). Sort gates were set based on unmutated TnI 19C7 binding for each condition with a gate set to sort full-length TnI binding clones. Each sort collected the top 0.1% of the TnI binding population. Sorted cells were grown in selective glucose media for 18-24 hours at 30° C. Sort 1 cells were induced and sorting was repeated for one additional round.

After the last sort, sorted cells were plated onto selective glucose plates and placed at 30° C. for 72 hours. Individual yeast colonies from these libraries were inoculated in selective glucose media, cryopreserved and induced in selective galactose media. Individual colonies were then characterized and ranked in an off-rate assay. TnI 19C7 AM1, AM2, and AM3 were isolated and identified from this combinatorial library.

Analysis of Selected TnI 19C7 Variants

Selected clones were initially characterized for improvements in KD as described above for wild type TnI 19C7 scFv. FIG. 9 shows the scFv KD values determined for four selected clones. The TnI 19C7 AM1 clone exhibited the most improved binding at 0.36 nM compared to the wild-type TnI 19C7 antibody 1.7 nM.

Selected TnI 19C7 scFv variants were sequenced to determine the amino acid mutations being expressed. Initially, plasmid DNA was isolated from yeast suspension cultures using a yeast mini-prep kit (Cat No. D2001, Zymo Research Orange, Calif.). In order to obtain sequencing grade plasmid DNA, plasmid from the yeast mini-prep kit was transformed into DH5α E. coli, and then purified from culture using E. coli mini-prep kits (Qiagen). Pure plasmid DNA was then sequenced using pYD41 vector specific primers (pYD41 for-TAGCATGACTGGTGGACAGC (SEQ ID NO:59) and pYD41rev-CGTAGAATCGAGACCGAG (SEQ ID NO:60)) Amino acid sequence data for TnI 19C7 scFv variants is shown in FIG. 13. Position numbers refers to amino acid position in the respective CDR (as numbered using Kabat method).

Overall the source of sequence diversity from the wild-type clone was found in the CDR L2 and CDR H1, whereas CDR L1 and H3 folded into a consensus motif. The CDR L3 and CDR H2 remained unmutated. The sequence data for CDR H1 indicated a preference for a conservative change at position 34 from isoleucine to leucine as identified in the 3 clones isolated from the combinatorial library. The consensus sequence for CDR H3 indicated a strong preference at position 100a for tyrosine instead of tryptophan, at position 101 for threonine instead of alanine, and at position 102 for aspartate instead of tyrosine as identified in the 3 clones isolated from the combinatorial library. From the master CDR sorting in which clone 19C7 AM4 was identified, the CDR H3 was the only CDR with mutations that were different than the combinatorial consensus set of sequences. Specifically the mutations were Ala96Phe, Tyr99Ser, Trp100aAla, and Tyr102Asp.

The consensus sequence data for CDR L1 indicated a preference for threonine at position 25, lysine at position 27, asparagine at position 28, valine at position 29, and histidine at position 34. For the CDR L2, each clone has unique or no mutations with only TnI 19C7 AM1 and AM2 sharing only the Ser54Arg mutation.

Cloning and Soluble Expression of TnI 19C7 Chimeric Antibodies in a Transient or Stable Expression System Selected TnI 19C7 variants were converted to chimeric mouse-mouse $IgG_{2\alpha}$/mouse kappa and/or mouse-human $IgG_1$/human kappa antibodies through cloning of the TnI 19C7 variable domains into the transient expression vector system called pBOS (Abbott Bioresearch Center, Worcester, Mass.). More specifically, PCR was used to amplify the variable heavy and variable light chain genes with restriction sites for cloning into separate pBOS vectors (Mizushima and Nagata, Nucleic Acids Research, 18:5322 (1990)). The variable heavy and variable light genes were ligated in digested and dephosphorylated vector and transformed into DH5α E. coli. Plasmid DNA was purified from E. coli and transfected into 293H cells using PEI (1 mg/ml). Transient antibody was expressed for the following TnI 19C7 variants: TnI 19C7 wt, AM1, AM2, AM3 and AM4.

For example, using the pBOS-TnI 19C7 AM1 heavy and light vectors, a stable CHO cell line plasmid was created in a two-step cloning procedure. First, variable heavy chain and variable light genes were ligated in frame to the human constant genes in pBV and pJV plasmids (Abbott Bioresearch Center, Worcester, Mass.), respectively, using the restriction enzymes SrfI/NotI. Ligation reactions were transformed into DH5α E. coli and plasmid DNA was subsequently isolated from individual colonies. The pBV-TnI 19C7 mouse variable heavy-human IgG1 and pJV-TnI 19C7 mouse variable light-human kappa were sequenced at the cloning sites.

The second cloning step involved combining the heavy chain $IgG_1$ genes and the light chain kappa genes into a single stable cell line vector. The pBV-TnI 19C7 AM1 human IgG1 and pJV-TnI 19C7 AM1 human kappa vectors were digested with AscI/PacI. The VL-human kappa constant and the VH-human IgG1 constant DNA fragments were gel purified and ligated to produce the stable cell line vector called pBJ-TnI 19C7 AM1. The pBJ-TnI 19C7 AM1 human heavy/light chimeric plasmid was transformed into CHO cells using a lipofectamine (Invitrogen) protocol. Stable cell lines were subcloned from initial transformation. A stable CHO cell line has been developed for the clone AM1 (also referred to as "TnI 19C7AM1 hG1kCHO204") and was deposited with the American Type Culture Collection, 10801 University Boulevard, Manassas, Va. 20110-2209 on Feb. 11, 2009 and received deposit designation PTA-9816.

Example II

Relative Affinity of Troponin I Clone 19C7 Wild Type and Affinity Matured Antibodies Troponin I clone 19C7 wild type (full mouse construct) and affinity matured (human constant region) antibodies were evaluated for relative affinity in a microtiter enzyme immunoassay. 96-well assay plates (NUNC Corporation, Rochester, N.Y.) were coated by adding 100 uL/well of a 2 ug/mL solution of either sheep anti-mouse IgG Fcγ specific antibody (Jackson ImmunoResearch, West Grove, Pa.) or donkey anti-human IgG Fcγ fragment specific antibody (Jackson ImmunoResearch). Both antibodies were diluted in phosphate buffered saline (PBS, Abbott Laboratories, Abbott Park, Ill.). The assay plates were incubated overnight at 15-30 deg C. The next day the coating reagent was removed and 200 uL/well of BSA solution (bovine serum albumin [Abbott Laboratories] diluted in PBS) was added. The BSA solution was incubated in the assay wells for 30 minutes at 15-30 deg C., removed and the assay wells washed by adding 300 uL/well distilled water (dH2O, Abbott Laboratories) and aspirating for three wash cycles. Next, 100 uL/well test samples were added. Test samples were prepared by creating an initial 2 ug/mL solution (in BSA solution) of each antibody, followed by log 3 dilutions, in BSA solution. The test samples were incubated for 2-3 hours at 15-30 deg C. after which they were aspirated away and the wells washed with dH2O as described above. Next, 100 uL/well of test antigen solutions were added to each assay well. The test antigen solutions were created by first preparing a 1000 ng/mL solution of scTnI-C-2 (aa 28-100 of cardiac troponin I linked to full length cardiac troponin C, Spectral Diagnostics) in BSA solution, followed by log 2 dilutions. The antigen solutions were incubated in the assay wells for 10 minutes at 15-30 deg C. and then removed by slapping out the solutions. The assay plates were then washed with dH2O as previously described. Next, 100 uL/well of biotin labeled goat anti-troponin I antibody (HyTest, diluted to 500 ng/mL in BSA solution) was added to each assay well and incubated for 30 minutes at 15-30 deg C. The antibody was then aspirated away and the wells washed with dH2O as described. Next, 100 uL/well of a 200 ng/mL solution (in BSA solution) of horse radish peroxidase labeled streptavidin (SA-HRPO, Jackson ImmunoResearch) was added and incubated for 30 minutes at 15-30 deg C. The SA-HRPO reagent was then aspirated away and the plates washed as described. Next, substrate solution was prepared by dissolving 1 OPD tablet per 10 mL OPD diluent (o-phenylenediamine, both Abbott Laboratories). 100 uL/well of the prepared substrate solution was added to the assay plates, incubated for about 4-5 minutes and then the reaction quenched by adding 100 uL/well 1N sulfuric acid (Abbott Laboratories). The resulting signal was read at 492 nm using an optical fluorometer. Results from the experiment were plotted using kaleidagraph software. The $Ag_{50}$ value (the concentration of antigen at 50% of maximal binding) was determined and used to compare the antibodies for relative affinity to the tested antigen.

Example III

Use of Monoclonal Antibody 19C7 in an Immunoassay

Troponin I clone 19C7 wild type (full mouse construct) and affinity matured (human constant region) antibodies were evaluated for relative affinity on the ARCHITECT® immunoassay analyzer (Abbott Laboratories). The assay was fully automated, and the analyzer performs all steps. Magnetic microparticles coated with a mouse anti-troponin I antibody (Abbott Laboratories, Abbott Park, Ill.) were mixed with varying levels of scTnI-C-2 (aa 28-100 of cardiac troponin I linked to full length cardiac troponin C (Spectral Diagnostics) and incubated for 18 minutes at 15-30 deg C. During this time, the microparticle coated antibody bound the scTnI-C-2. The microparticles were then attracted to a magnet, the remaining assay solution was aspirated, and the particles washed with assay diluent (Abbott Laboratories, Abbott Park, Ill.). Next, the wild type or affinity matured 19C7 antibodies, all of which were labeled with acridinium (Abbott Laboratories, Abbott Park, Ill.) were added to the microparticles and incubated for 4 minutes at 15-30 deg C. Next, the microparticles were attracted to a magnet, the remaining assay solution was aspirated, and the particles were washed with assay diluent. Signal (relative light units) was generated by the addition of pre-trigger and trigger solutions (both Abbott Laboratories). Signal ratios were calculated and used to compare antibodies. As can be established based upon the results shown in FIG. 11, AM1 antibody gave a better signal than wild-type antibody.

SEQUENCE LISTING

<160> NUMBER OF SEQ ID NOS: 112

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1 gaattcgcgg cccagccggc catggccgag gtccagcttc agcagtca 48

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2 cttcaggggc gtcaactcct tggcgggacc tgcagagaca gtgac 45

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 3 ttgacgcccc tgaaggaggc gaaggtctct gacatcttgc tgact 45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 gaagggccct ctagactcga gggcggccgc ccgttttatt tccag 45

<210> SEQ ID NO 5
<211> LENGTH: 91
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5 gaaacctggg gcctcagtga ggatatcctg caaggcttct ggatacacat tcactgacta 60 caacatacac tgggtgaaac agagccatgg a 91

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6 agaagccttg caggatatcc tcactgaggc 30

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7 agtaacgttt gtcagtaatt gc 22

<210> SEQ ID NO 8
<211> LENGTH: 108
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8 agccatggaa agagccttga gtggattgga tatatttatc cttacaatgg tattactggc 60 tacaaccaga aattcaagag caaggccaca ttgactgtag acagttcc 108

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9 tccaatccac tcaaggctct ttccatggct 30

<210> SEQ ID NO 10
<211> LENGTH: 92
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10 catctgagga ctctgcagtc tatttttgtg ctagagacgc ttatgattac gactggttgg 60 cttactgggg ccaagggact ctggtcactg tc 92

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11 tctagcacaa aaatagactg cagagtcctc 30

<210> SEQ ID NO 12
<211> LENGTH: 95
<212> TYPE: DNA
<213> ORGANISM: Artificial Sequence <220> FEATURE:
<223> OTHER INFORMATION: Description of Artificial Sequence: Synthetic
primer

<400> SEQUENCE: 12 ctgtgagtcc aggagaaaga gtcagtttct cctgcagggc cagtcagagc attggcacaa 60 acatatattg gtatcagcaa agaacaaatg gttct 95

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13 gcaggagaaa ctgactcttt ctcctggact 30

<210> SEQ ID NO 14
<211> LENGTH: 83
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14 aaagaacaaa tggttctcca aggcttctca taaagtatgc ttctgagtct atctctggga 60 tcccttccag gtttagtggc agt 83

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15 ctttatgaga agccttggag aaccatt 27

<210> SEQ ID NO 16
<211> LENGTH: 88
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16 gtgtggagtc tgaagatatt gctgattatt actgtcaaca aataataact ggccatacac 60 gttcggaggg gggaccaagc tggaaata 88

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17 acagtaataa tcagcaatat cttcaga 27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18 atagaaaagg atattacatg ggaaaac 27

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19 tgggtgaaac agagccatgg aaagagcctt 30

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20 aaggccacat tgactgtaga cagtt 25

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21 tggtatcagc aaagaaca 18

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22 gggatccctt ccaggtttag tggc 24

<210> SEQ ID NO 23
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(357)

<400> SEQUENCE: 23

```
gag gtc cag ctt cag cag tca gga cct gac ctg gtg aaa cct ggg gcc       48
Glu Val Gln Leu Gln Gln Ser Gly Pro Asp Leu Val Lys Pro Gly Ala
1               5                   10                  15

tca gtg agg ata tcc tgc aag gct tct gga tac aca ttc acg gac tat       96
Ser Val Arg Ile Ser Cys Lys Ala Ser Gly Tyr Thr Phe Thr Asp Tyr
            20                  25                  30

aac tta cac tgg gtg aaa cag agc cat gga aag agc ctt gag tgg att      144
Asn Leu His Trp Val Lys Gln Ser His Gly Lys Ser Leu Glu Trp Ile
        35                  40                  45

gga tat att tat cct tac aat ggt att act ggc tac aac cag aaa ttc      192
Gly Tyr Ile Tyr Pro Tyr Asn Gly Ile Thr Gly Tyr Asn Gln Lys Phe
    50                  55                  60

aag agc aag gcc aca ttg act gta gac agt tcc tcc aat aca gcc tac      240
Lys Ser Lys Ala Thr Leu Thr Val Asp Ser Ser Ser Asn Thr Ala Tyr
65                  70                  75                  80

atg gac ctc cgc agc ctg aca tct gag gac tct gca gtc tat ttt tgt      288
Met Asp Leu Arg Ser Leu Thr Ser Glu Asp Ser Ala Val Tyr Phe Cys
                85                  90                  95

gct aga gac gct tat gat tac gac tat ctg acg gac tgg ggc caa ggg      336
Ala Arg Asp Ala Tyr Asp Tyr Asp Tyr Leu Thr Asp Trp Gly Gln Gly
            100                 105                 110

act ctg gtc act gtc agc gct                                          357
Thr Leu Val Thr Val Ser Ala
        115
```

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Gln Gln Ser Gly Pro Asp Leu Val Lys Pro Gly Ala
1               5                   10                  15

Ser Val Arg Ile Ser Cys Lys Ala Ser Gly Tyr Thr Phe Thr Asp Tyr
            20                  25                  30

Asn Leu His Trp Val Lys Gln Ser His Gly Lys Ser Leu Glu Trp Ile
        35                  40                  45

Gly Tyr Ile Tyr Pro Tyr Asn Gly Ile Thr Gly Tyr Asn Gln Lys Phe
    50                  55                  60

Lys Ser Lys Ala Thr Leu Thr Val Asp Ser Ser Ser Asn Thr Ala Tyr
65                  70                  75                  80

Met Asp Leu Arg Ser Leu Thr Ser Glu Asp Ser Ala Val Tyr Phe Cys
                85                  90                  95

Ala Arg Asp Ala Tyr Asp Tyr Asp Tyr Leu Thr Asp Trp Gly Gln Gly
            100                 105                 110

Thr Leu Val Thr Val Ser Ala
        115
```

<210> SEQ ID NO 25
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25 ctccaggtcg aagtcgtcag tcctggactg gaccactttg gaccccggag tcactcctat 60 aggacgttcc gaagacctat gtgtaagtgc ctgatattga atgtgaccca ctttgtctcg 120 gtacctttct cggaactcac ctaacctata taaataggaa tgttaccata atgaccgatg 180 ttggtcttta agttctcgtt ccggtgtaac tgacatctgt caaggaggtt atgtcggatg 240 tacctggagg cgtcggactg tagactcctg agacgtcaga taaaaacacg atctctgcga 300 atactaatgc tgatagactg cctgaccccg gttccctgag accagtgaca gtcgcga 357

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Glu Val Gln Leu Gln Gln Ser Gly Pro Asp Leu Val Lys Pro Gly Ala
1 5 10 15

Ser Val Arg Ile Ser Cys Lys Ala Ser Gly Tyr Thr Phe Thr Asp Tyr
20 25 30

Asn Leu His Trp Val Lys Gln Ser His Gly Lys Ser Leu Glu Trp Ile
35 40 45

Gly Tyr Ile Tyr Pro Tyr Asn Gly Ile Thr Gly Tyr Asn Gln Lys Phe
50 55 60

Lys Ser Lys Ala Thr Leu Thr Val Asp Ser Ser Ser Asn Thr Ala Tyr
65 70 75 80

Met Asp Leu Arg Ser Leu Thr Ser Glu Asp Ser Ala Val Tyr Phe Cys
85 90 95

Ala Arg Asp Ala Tyr Asp Tyr Asp Tyr Leu Thr Asp Trp Gly Gln Gly
100 105 110

Thr Leu Val Thr Val Ser Ala
115

<210> SEQ ID NO 27
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(324)

<400> SEQUENCE: 27 gac atc ttg ctg act cag tca tcc agt ctc ctg tct gtg agt cca gga 48
Asp Ile Leu Leu Thr Gln Ser Ser Ser Leu Leu Ser Val Ser Pro Gly
1 5 10 15 gaa aga gtc agt ttc tcc tgc agg acc agt aag aac gtt ggc aca aac 96
Glu Arg Val Ser Phe Ser Cys Arg Thr Ser Lys Asn Val Gly Thr Asn
20 25 30 att cat tgg tat cag caa aga aca aat ggt tct cca agg ctt ctc ata 144
Ile His Trp Tyr Gln Gln Arg Thr Asn Gly Ser Pro Arg Leu Leu Ile
35 40 45 aag tat gct tca gag cgt tta cct ggg atc cct tcc agg ttt agt ggc 192
Lys Tyr Ala Ser Glu Arg Leu Pro Gly Ile Pro Ser Arg Phe Ser Gly
50 55 60

```
agt ggg tca ggg aca gat ttt act ctt agc atc aac agt gtg gag tct      240
Ser Gly Ser Gly Thr Asp Phe Thr Leu Ser Ile Asn Ser Val Glu Ser
65                  70                  75                  80

gaa gat att gct gat tat tac tgt caa caa agt aat aac tgg cca tac      288
Glu Asp Ile Ala Asp Tyr Tyr Cys Gln Gln Ser Asn Asn Trp Pro Tyr
                85                  90                  95

acg ttc gga ggg ggg acc aag ctg gaa ata aaa cgg                      324
Thr Phe Gly Gly Gly Thr Lys Leu Glu Ile Lys Arg
            100                 105


<210> SEQ ID NO 28
<211> LENGTH: 108
<212> TYPE: PRT
<213> ORGANISM: Artificial Sequence
<220> FEATURE:
<223> OTHER INFORMATION: Synthetic Construct

<400> SEQUENCE: 28

Asp Ile Leu Leu Thr Gln Ser Ser Ser Leu Leu Ser Val Ser Pro Gly
1               5                   10                  15

Glu Arg Val Ser Phe Ser Cys Arg Thr Ser Lys Asn Val Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Arg Leu Pro Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Tyr
                85                  90                  95

Thr Phe Gly Gly Gly Thr Lys Leu Glu Ile Lys Arg
            100                 105


<210> SEQ ID NO 29
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

ctgtagaacg actgagtcag aggtcagtag gacagacact caggtcctct ttctcagtca     60

aagaggacgt cctggtcatt cttgcaaccg tgtttgtaag taaccatagt cgtttcttgt    120

ttaccaagag gttccgaaga gtatttcata cgaagtctcg caaatggacc ctagggaagg    180

tccaaatcac cgtcacccag tccctgtcta aaatgagaat cgtagttgtc acacctcaga    240

cttctataac gactaataat gacagttgtt tcattattga ccggtatgtg caagcctccc    300

ccctggttcg acctttattt tgcc                                           324


<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 30

Asp Ile Leu Leu Thr Gln Ser Ser Ser Leu Leu Ser Val Ser Pro Gly
1 5 10 15

Glu Arg Val Ser Phe Ser Cys Arg Thr Ser Lys Asn Val Gly Thr Asn
20 25 30

Ile His Trp Tyr Gln Gln Arg Thr Asn Gly Ser Pro Arg Leu Leu Ile
35 40 45

Lys Tyr Ala Ser Glu Arg Leu Pro Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Ser Asn Asn Trp Pro Tyr
85 90 95

Thr Phe Gly Gly Gly Thr Lys Leu Glu Ile Lys Arg
100 105

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 31

His His His His His His
1 5

<210> SEQ ID NO 32
<211> LENGTH: 10
<212> TYPE: PRT
<213> ORGANISM: Unknown
<220> FEATURE:
<223> OTHER INFORMATION: Description of Unknown: Unknown wild-type
peptide

<400> SEQUENCE: 32

Gly Tyr Thr Phe Thr Asp Tyr Asn Ile His
1 5 10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gly Tyr Thr Phe Thr Asp Tyr Asn Leu His
1 5 10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Gly Tyr Thr Phe Thr Asp Tyr Asn Leu His
1 5 10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Gly Tyr Ser Phe Thr Asp Tyr Asn Leu His
1 5 10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Gly Tyr Thr Phe Thr Asp Tyr Asn Ile His
1 5 10

<210> SEQ ID NO 37
<211> LENGTH: 10
<212> TYPE: PRT
<213> ORGANISM: Unknown
<220> FEATURE:
<223> OTHER INFORMATION: Description of Unknown: Unknown wild-type
peptide

<400> SEQUENCE: 37

Asp Ala Tyr Asp Tyr Asp Trp Leu Ala Tyr
1 5 10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Asp Ala Tyr Asp Tyr Asp Tyr Leu Thr Asp
1 5 10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Asp Ala Tyr Asp Tyr Asp Tyr Leu Thr Asp
1 5 10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Asp Ala Tyr Asp Tyr Asp Tyr Leu Thr Asp
1 5 10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Asp Phe Tyr Asp Ser Asp Ala Leu Ala Asp
1 5 10

<210> SEQ ID NO 42
<211> LENGTH: 11
<212> TYPE: PRT
<213> ORGANISM: Unknown
<220> FEATURE:
<223> OTHER INFORMATION: Description of Unknown: Unknown wild-type
peptide

<400> SEQUENCE: 42

Arg Ala Ser Gln Ser Ile Gly Thr Asn Ile Tyr
1 5 10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Arg Thr Ser Lys Asn Val Gly Thr Asn Ile His
1 5 10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Arg Thr Ser Lys Asn Val Gly Thr Asn Ile His
1 5 10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Arg Thr Ser Lys Asn Val Gly Thr Asn Ile His
1 5 10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Arg Ala Ser Gln Ser Ile Gly Thr Asn Ile Tyr
1 5 10

<210> SEQ ID NO 47
<211> LENGTH: 7
<212> TYPE: PRT
<213> ORGANISM: Unknown
<220> FEATURE:
<223> OTHER INFORMATION: Description of Unknown: Unknown wild-type
peptide

<400> SEQUENCE: 47

Tyr Ala Ser Glu Ser Ile Ser
1 5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Tyr Ala Ser Glu Arg Leu Pro
1 5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Tyr Gly Thr Glu Arg Val Phe
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Tyr Ala Ser Glu Ser Ile Ser
1 5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Tyr Ala Ser Glu Ser Ile Ser
1 5

<210> SEQ ID NO 52
<211> LENGTH: 330
<212> TYPE: PRT
<213> ORGANISM: Homo sapiens

<400> SEQUENCE: 52

Ala Ser Thr Lys Gly Pro Ser Val Phe Phe Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Gly Tyr Thr Phe Thr Asp Tyr Asn Leu His
1 5 10

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Tyr Ile Tyr Pro Tyr Asn Gly Ile Thr Gly Tyr Asn Gln Lys Phe Lys
1 5 10 15

Ser

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Asp Ala Tyr Asp Tyr Asp Leu Thr Asp
1 5

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Arg Thr Ser Lys Asn Val Gly Thr Asn Ile His
1 5 10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Tyr Ala Ser Glu Arg Leu Pro
1 5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gln Gln Ser Asn Asn Trp Pro Tyr Thr
1 5

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Gly Pro Ala Lys Glu Leu Thr Pro Leu Lys Glu Ala Lys Val Ser
1 5 10 15

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61 tagcatgact ggtggacagc 20

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62 cgtagaatcg agaccgag 18

<210> SEQ ID NO 63
<211> LENGTH: 106
<212> TYPE: PRT
<213> ORGANISM: Homo sapiens

<400> SEQUENCE: 63

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 64
<211> LENGTH: 105
<212> TYPE: PRT
<213> ORGANISM: Homo sapiens

<400> SEQUENCE: 64

Gln Pro Lys Ala Ala Pro Ser Val Thr Leu Phe Pro Pro Ser Ser Glu
1 5 10 15

Glu Leu Gln Ala Asn Lys Ala Thr Leu Val Cys Leu Ile Ser Asp Phe
20 25 30

Tyr Pro Gly Ala Val Thr Val Ala Trp Lys Ala Asp Ser Ser Pro Val
35 40 45

Lys Ala Gly Val Glu Thr Thr Thr Pro Ser Lys Gln Ser Asn Asn Lys
50 55 60

Tyr Ala Ala Ser Ser Tyr Leu Ser Leu Thr Pro Glu Gln Trp Lys Ser
65 70 75 80

His Arg Ser Tyr Ser Cys Gln Val Thr His Glu Gly Ser Thr Val Glu
85 90 95

Lys Thr Val Ala Pro Thr Glu Cys Ser
100 105

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (9)..(9)
<223> OTHER INFORMATION: Ile or Leu

<400> SEQUENCE: 65

Gly Tyr Xaa Phe Thr Asp Tyr Asn Xaa His
1 5 10

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Tyr Ile Tyr Pro Tyr Asn Gly Ile Thr Gly Tyr Asn Gln Lys Phe Lys
1 5 10 15

Ser

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Ala or Phe
<220> FEATURE:
<221> NAME/KEY: MOD_RES
<222> LOCATION: (5)..(5)
<223> OTHER INFORMATION: Tyr or Ser <220> FEATURE:
<221> NAME/KEY: MOD_RES
<222> LOCATION: (7)..(7)
<223> OTHER INFORMATION: Trp, Tyr or Ala
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (10)..(10)
<223> OTHER INFORMATION: Tyr or Asp

<400> SEQUENCE: 67

Asp Xaa Tyr Asp Xaa Asp Xaa Leu Xaa Xaa
1 5 10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (4)..(4)
<223> OTHER INFORMATION: Gln or Lys
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Tyr or His

<400> SEQUENCE: 68

Arg Xaa Ser Xaa Xaa Xaa Gly Thr Asn Ile Xaa
1 5 10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Ser or Arg
<220> FEATURE:
<221> NAME/KEY: MOD_RES
<222> LOCATION: (6)..(6)
<223> OTHER INFORMATION: Ile, Leu or Val <220> FEATURE:
<221> NAME/KEY: MOD_RES
<222> LOCATION: (7)..(7)
<223> OTHER INFORMATION: Ser, Pro or Phe

<400> SEQUENCE: 69

Tyr Xaa Xaa Glu Xaa Xaa Xaa
1 5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Gln Gln Ser Asn Asn Trp Pro Tyr Thr
1 5

<210> SEQ ID NO 71
<211> LENGTH: 30
<212> TYPE: PRT
<213> ORGANISM: Mus sp.

<400> SEQUENCE: 71

Glu Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser
20 25 30

<210> SEQ ID NO 72
<211> LENGTH: 14
<212> TYPE: PRT
<213> ORGANISM: Mus sp.

<400> SEQUENCE: 72

Trp Ile Arg Gln Pro Pro Gly Lys Ala Leu Glu Trp Leu Ala
1 5 10

<210> SEQ ID NO 73
<211> LENGTH: 32
<212> TYPE: PRT
<213> ORGANISM: Mus sp.

<400> SEQUENCE: 73

Arg Leu Thr Ile Ser Lys Asp Thr Ser Lys Asn Gln Val Val Leu Thr
1 5 10 15

Met Thr Asn Met Asp Pro Val Asp Thr Ala Thr Tyr Tyr Cys Ala Arg
20 25 30

<210> SEQ ID NO 74
<211> LENGTH: 11
<212> TYPE: PRT
<213> ORGANISM: Mus sp.

<400> SEQUENCE: 74

Trp Gly Gln Gly Thr Thr Val Thr Val Ser Ser
1 5 10

<210> SEQ ID NO 75
<211> LENGTH: 30
<212> TYPE: PRT
<213> ORGANISM: Mus sp.

<400> SEQUENCE: 75

Glu Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser
20 25 30

<210> SEQ ID NO 76
<211> LENGTH: 14
<212> TYPE: PRT
<213> ORGANISM: Mus sp.

<400> SEQUENCE: 76

Trp Ile Arg Gln Pro Pro Gly Lys Ala Leu Glu Trp Leu Ala
1 5 10

<210> SEQ ID NO 77
<211> LENGTH: 32
<212> TYPE: PRT
<213> ORGANISM: Mus sp.

<400> SEQUENCE: 77

Arg Leu Thr Ile Ser Lys Asp Thr Ser Lys Ser Gln Val Val Leu Thr
1 5 10 15

Met Thr Asn Met Asp Pro Val Asp Thr Ala Thr Tyr Tyr Cys Ala Arg
20 25 30

<210> SEQ ID NO 78
<211> LENGTH: 11
<212> TYPE: PRT
<213> ORGANISM: Mus sp.

<400> SEQUENCE: 78

Trp Gly Gln Gly Thr Thr Val Thr Val Ser Ser
1 5 10

<210> SEQ ID NO 79
<211> LENGTH: 30
<212> TYPE: PRT
<213> ORGANISM: Mus sp.

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 80
<211> LENGTH: 14
<212> TYPE: PRT
<213> ORGANISM: Mus sp.

<400> SEQUENCE: 80

Trp Val Arg Gln Ala Pro Gly Lys Gly Leu Glu Trp Val Gly
1 5 10

<210> SEQ ID NO 81
<211> LENGTH: 32
<212> TYPE: PRT
<213> ORGANISM: Mus sp.

<400> SEQUENCE: 81

Arg Phe Thr Ile Ser Arg Asp Asp Ser Lys Asn Ser Leu Tyr Leu Gln
1 5 10 15

Met Asn Ser Leu Lys Thr Glu Asp Thr Ala Val Tyr Tyr Cys Ala Arg
20 25 30

<210> SEQ ID NO 82
<211> LENGTH: 11
<212> TYPE: PRT
<213> ORGANISM: Mus sp.

<400> SEQUENCE: 82

Trp Gly Gln Gly Thr Thr Val Thr Val Ser Ser
1 5 10

<210> SEQ ID NO 83
<211> LENGTH: 30
<212> TYPE: PRT
<213> ORGANISM: Mus sp.

<400> SEQUENCE: 83

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser
20 25 30

<210> SEQ ID NO 84
<211> LENGTH: 14
<212> TYPE: PRT
<213> ORGANISM: Mus sp.

<400> SEQUENCE: 84

Trp Val Arg Gln Ala Pro Gly Lys Gly Leu Glu Trp Val Ser
1 5 10

<210> SEQ ID NO 85
<211> LENGTH: 32
<212> TYPE: PRT
<213> ORGANISM: Mus sp.

<400> SEQUENCE: 85

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 86
<211> LENGTH: 11
<212> TYPE: PRT
<213> ORGANISM: Mus sp.

<400> SEQUENCE: 86

Trp Gly Gln Gly Thr Thr Val Thr Val Ser Ser
1 5 10

<210> SEQ ID NO 87
<211> LENGTH: 30
<212> TYPE: PRT
<213> ORGANISM: Mus sp.

<400> SEQUENCE: 87

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser
20 25 30

<210> SEQ ID NO 88
<211> LENGTH: 14
<212> TYPE: PRT
<213> ORGANISM: Mus sp.

<400> SEQUENCE: 88

Trp Val Arg Gln Ala Pro Gly Gln Gly Leu Glu Trp Met Gly
1 5 10

<210> SEQ ID NO 89
<211> LENGTH: 32
<212> TYPE: PRT
<213> ORGANISM: Mus sp.

<400> SEQUENCE: 89

Arg Val Thr Ile Thr Ala Asp Lys Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 90
<211> LENGTH: 11
<212> TYPE: PRT
<213> ORGANISM: Mus sp.

<400> SEQUENCE: 90

Trp Gly Gln Gly Thr Thr Val Thr Val Ser Ser
1 5 10

<210> SEQ ID NO 91
<211> LENGTH: 30
<212> TYPE: PRT
<213> ORGANISM: Mus sp.

<400> SEQUENCE: 91

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 92
<211> LENGTH: 14
<212> TYPE: PRT
<213> ORGANISM: Mus sp.

<400> SEQUENCE: 92

Trp Val Arg Gln Ala Pro Gly Gln Gly Leu Glu Trp Met Gly
1 5 10

<210> SEQ ID NO 93
<211> LENGTH: 32
<212> TYPE: PRT
<213> ORGANISM: Mus sp.

<400> SEQUENCE: 93

Arg Val Thr Met Thr Thr Asp Thr Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 94
<211> LENGTH: 11
<212> TYPE: PRT
<213> ORGANISM: Mus sp.

<400> SEQUENCE: 94

Trp Gly Gln Gly Thr Thr Val Thr Val Ser Ser
1 5 10

<210> SEQ ID NO 95
<211> LENGTH: 23
<212> TYPE: PRT
<213> ORGANISM: Mus sp.

<400> SEQUENCE: 95

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 96
<211> LENGTH: 15
<212> TYPE: PRT
<213> ORGANISM: Mus sp.

<400> SEQUENCE: 96

Trp Tyr Gln Gln Lys Pro Gly Gln Pro Pro Lys Leu Leu Ile Tyr
1 5 10 15

<210> SEQ ID NO 97
<211> LENGTH: 32
<212> TYPE: PRT
<213> ORGANISM: Mus sp.

<400> SEQUENCE: 97

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 98
<211> LENGTH: 11
<212> TYPE: PRT
<213> ORGANISM: Mus sp.

<400> SEQUENCE: 98

Phe Gly Gly Gly Thr Lys Val Glu Ile Lys Arg
1 5 10

<210> SEQ ID NO 99
<211> LENGTH: 23
<212> TYPE: PRT
<213> ORGANISM: Mus sp.

<400> SEQUENCE: 99

Glu Ile Val Met Thr Gln Ser Pro Ala Thr Leu Ser Val Ser Pro Gly
1 5 10 15

Glu Arg Ala Thr Leu Ser Cys
20

<210> SEQ ID NO 100
<211> LENGTH: 15
<212> TYPE: PRT
<213> ORGANISM: Mus sp.

<400> SEQUENCE: 100

Trp Tyr Gln Gln Lys Pro Gly Gln Ala Pro Arg Leu Leu Ile Tyr
1 5 10 15

<210> SEQ ID NO 101
<211> LENGTH: 32
<212> TYPE: PRT
<213> ORGANISM: Mus sp.

<400> SEQUENCE: 101

Gly Ile Pro Ala Arg Phe Ser Gly Ser Gly Ser Gly Thr Glu Phe Thr
1 5 10 15

Leu Thr Ile Ser Ser Leu Gln Ser Glu Asp Phe Ala Val Tyr Tyr Cys
20 25 30

<210> SEQ ID NO 102
<211> LENGTH: 11
<212> TYPE: PRT
<213> ORGANISM: Mus sp.

<400> SEQUENCE: 102

Phe Gly Gly Gly Thr Lys Val Glu Ile Lys Arg
1 5 10

<210> SEQ ID NO 103
<211> LENGTH: 23
<212> TYPE: PRT
<213> ORGANISM: Mus sp.

<400> SEQUENCE: 103

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 104
<211> LENGTH: 15
<212> TYPE: PRT
<213> ORGANISM: Mus sp.

<400> SEQUENCE: 104

Trp Tyr Gln Gln Lys Pro Glu Lys Ala Pro Lys Ser Leu Ile Tyr
1 5 10 15

<210> SEQ ID NO 105
<211> LENGTH: 32
<212> TYPE: PRT
<213> ORGANISM: Mus sp.

<400> SEQUENCE: 105

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 106
<211> LENGTH: 11
<212> TYPE: PRT
<213> ORGANISM: Mus sp.

<400> SEQUENCE: 106

Phe Gly Gly Gly Thr Lys Val Glu Ile Lys Arg
1 5 10

<210> SEQ ID NO 107
<211> LENGTH: 23
<212> TYPE: PRT
<213> ORGANISM: Mus sp.

<400> SEQUENCE: 107

Asp Ile Gln Met Thr Gln Ser Pro Ser Ser Val Ser Ala Ser Val Gly
1 5 10 15

Asp Arg Val Thr Ile Thr Cys
20

<210> SEQ ID NO 108
<211> LENGTH: 15
<212> TYPE: PRT
<213> ORGANISM: Mus sp.

<400> SEQUENCE: 108

Trp Tyr Gln Gln Lys Pro Gly Lys Ala Pro Lys Leu Leu Ile Tyr
1 5 10 15

<210> SEQ ID NO 109
<211> LENGTH: 32
<212> TYPE: PRT
<213> ORGANISM: Mus sp.

<400> SEQUENCE: 109

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 110
<211> LENGTH: 11
<212> TYPE: PRT
<213> ORGANISM: Mus sp.

<400> SEQUENCE: 110

Phe Gly Gly Gly Thr Lys Val Glu Ile Lys Arg
1 5 10

<210> SEQ ID NO 111
<211> LENGTH: 726
<212> TYPE: DNA
<213> ORGANISM: Unknown
<220> FEATURE:
<223> OTHER INFORMATION: Description of Unknown: Unknown wild-type
polynucleotide

```
<400> SEQUENCE: 111

gaggtccagc ttcagcagtc aggacctgac ctggtgaaac ctggggcctc agtgaggata     60

tcctgcaagg cttctggata cacattcact gactacaaca tacactgggt gaaacagagc    120

catggaaaga gccttgagtg gattggatat atttatcctt acaatggtat tactggctac    180

aaccagaaat tcaagagcaa ggccacattg actgtagaca gttcctccaa tacagcctac    240

atggacctcc gcagcctgac atctgaggac tctgcagtct atttttgtgc tagagacgct    300

tatgattacg actggttggc ttactggggc caagggactc tggtcactgt ctctgcaggt    360

cccgccaagg agttgacgcc cctgaaggag gcgaaggtct ctgacatctt gctgactcag    420

tctccagtca tcctgtctgt gagtccagga gaaagagtca gtttctcctg cagggccagt    480

cagagcattg gcacaaacat atattggtat cagcaaagaa caaatggttc tccaaggctt    540

ctcataaagt atgcttctga gtctatctct gggatccctt ccaggtttag tggcagtggg    600

tcagggacag attttactct tagcatcaac agtgtggagt ctgaagatat tgctgattat    660

tactgtcaac aaagtaataa ctggccatac acgttcggag gggggaccaa gctggaaata    720

aaacgg                                                               726


<210> SEQ ID NO 112
<211> LENGTH: 726
<212> TYPE: DNA
<213> ORGANISM: Unknown
<220> FEATURE:
<223> OTHER INFORMATION: Description of Unknown: Unknown wild-type
      polynucleotide

<400> SEQUENCE: 112

ctccaggtcg aagtcgtcag tcctggactg gaccactttg gaccccggag tcactcctat     60

aggacgttcc gaagacctat gtgtaagtga ctgatgttgt atgtgaccca ctttgtctcg    120

gtacctttct cggaactcac ctaacctata taaataggaa tgttaccata atgaccgatg    180

ttggtcttta agttctcgtt ccggtgtaac tgacatctgt caaggaggtt atgtcggatg    240

tacctggagg cgtcggactg tagactcctg agacgtcaga taaaaacacg atctctgcga    300

atactaatgc tgaccaaccg aatgaccccg gttccctgag accagtgaca gagacgtcca    360

gggcggttcc tcaactgcgg ggacttcctc cgcttccaga gactgtagaa cgactgagtc    420

agaggtcagt aggacagaca ctcaggtcct ctttctcagt caaagaggac gtcccggtca    480

gtctcgtaac cgtgtttgta tataaccata gtcgtttctt gtttaccaag aggttccgaa    540

gagtatttca tacgaagact cagatagaga ccctagggaa ggtccaaatc accgtcaccc    600

agtccctgtc taaaatgaga atcgtagttg tcacacctca gacttctata acgactaata    660

atgacagttg tttcattatt gaccggtatg tgcaagcctc ccccctggtt cgacctttat    720

tttgcc                                                               726
```

What is claimed is:

1. A Chinese Hamster Ovary (CHO) cell line, referred to as TnI 19C7 AM1 hG1CHO 204, designated by American Type Culture Collection (ATCC) deposit Number PTA-9816.

[2. An isolated nucleic acid molecule encoding a binding protein, wherein the binding protein comprises a variable heavy chain, and wherein the amino acid sequence of the variable heavy chain of said binding protein has at least 90% identity to SEQ ID NO:25 and wherein said binding protein maintains the binding activity of SEQ ID NO:25.]

[3. The isolated nucleic acid molecule of claim 2, wherein the encoded binding protein further comprises a variable light chain, and wherein the amino acid sequence of the variable light chain of said binding protein has at least 90% identity to SEQ ID NO:28 and wherein said binding protein maintains the binding activity of SEQ ID NO:28.]

4. An isolated nucleic acid molecule encoding a binding protein, wherein the binding protein comprises a variable heavy chain, and wherein the amino acid sequence of the variable heavy chain of said binding protein is SEQ ID NO:25.

5. An isolated nucleic acid molecule encoding a binding protein, wherein the binding protein comprises a variable light chain, and wherein the amino acid sequence of the variable light chain of said binding protein is SEQ ID NO:28.

6. The isolated nucleic acid molecule of claim 5, wherein said encoded binding protein further comprises a variable heavy chain, and wherein the amino acid sequence of the variable heavy chain of said binding protein is SEQ ID NO:25.

7. A vector comprising said isolated nucleic acid molecule *wherein said isolated nucleic acid molecule encodes a binding protein, wherein said binding protein comprises the variable heavy chain* of claim 4 and *the variable light chain of* claim 5.

8. An isolated host cell comprising said vector of claim 7.

9. A method of producing a binding protein capable of binding to Troponin I, comprising culturing said host cell of claim 8 for a time and under conditions sufficient to produce said binding protein.

*10. A method of producing a Troponin I binding protein comprising culturing a host cell referred to as TnI 19C7 AM1 hG1 CHO 204, designated by American Type Culture Collection (ATCC) deposit Number PTA-9816 under conditions sufficient to produce said binding protein.*

*11. A method of producing a Troponin I binding protein comprising culturing a host cell that comprises a nucleic acid that encodes an antibody heavy chain that comprises a CDR1 sequence of SEQ ID NO:52, a CDR2 sequence of SEQ ID NO: 53, and a CDR3 sequence of SEQ ID NO:54, and a light chain that comprises a CDR1 sequence of SEQ ID NO:55, a CDR2 sequence of SEQ ID NO: 56, and a CDR3 sequence of SEQ ID NO:57 under conditions sufficient to produce said binding protein.*

*12. A method of producing a Troponin I binding protein comprising culturing a host cell that comprises a nucleic acids that encode the same heavy and light chains as the Chinese Hamster ovary cell referred to as TnI 19C7 AM1 hG1 CHO 204, designated by American Type Culture Collection (ATCC) deposit Number PTA-9816 under conditions sufficient to produce said binding protein.*

* * * * *